(12) United States Patent
Schlom et al.

(10) Patent No.: US 8,883,448 B2
(45) Date of Patent: *Nov. 11, 2014

(54) **MUTATED *RAS* PEPTIDES FOR GENERATION OF CD8⁺ CYTOTOXIC T LYMPHOCYTES**

(75) Inventors: Jeffrey Schlom, Potomac, MD (US); Scott Abrams, Amherst, NY (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 544 days.

This patent is subject to a terminal disclaimer.

(21) Appl. No.: 12/623,062

(22) Filed: Nov. 20, 2009

(65) Prior Publication Data

US 2010/0074945 A1    Mar. 25, 2010

Related U.S. Application Data

(63) Continuation of application No. 09/155,590, filed as application No. PCT/US97/06470 on Apr. 17, 1997, now Pat. No. 7,709,002, which is a continuation-in-part of application No. 08/635,344, filed on Apr. 19, 1996, now abandoned.

(51) Int. Cl.
  *C12N 15/11*  (2006.01)
  *C07H 21/04*  (2006.01)
  *C07K 14/82*  (2006.01)
  *A61K 39/00*  (2006.01)

(52) U.S. Cl.
  CPC *C07K 14/82* (2013.01); *A61K 39/00* (2013.01)
  USPC ......................................... 435/69.3; 536/23.1

(58) Field of Classification Search
  None
  See application file for complete search history.

(56) References Cited

U.S. PATENT DOCUMENTS

| | | | |
|---|---|---|---|
| 5,800,810 A | 9/1998 | Doyle et al. | |
| 5,861,372 A | 1/1999 | Folkman et al. | |
| 6,039,948 A | 3/2000 | Stevens | |

FOREIGN PATENT DOCUMENTS

| | | |
|---|---|---|
| EP | 0 429 816 A1 | 10/1989 |
| GB | 2253211 | 9/1992 |
| WO | WO 89/06974 | 8/1989 |
| WO | WO 92/14756 | 9/1992 |

OTHER PUBLICATIONS

Abstract of Wheeler (Salud p'ublica de M'exico, (Jul.-Aug. 1997) 39 (4) 283-7).*
Efferson et al (Anticancer research, 2005, vol. 25, pp. 715-724).*
Bachman et al (Journal of Immunology, 2005, vol. 175, pp. 4677-4685).*
Abrams et al., *Cell. Immunol.*, 182, 137-151 (1997).
Abrams et al., *Eur. J. Immunol.*, 25, 2588-2597 (1995).
Abrams et al., *Eur. J. Immunol.*, 26 (2), 435-443 (1996).
Abrams et al., "*ras* Oncogene Products as Tumor-Specific Antigens for Activation of T-Lymphocyte-MEdiated Immunity," *Gene Therapy of Cancer*, Chapter 16, 251-269 (1999).
Abrams et al., *Sem. Oncol.*, 23, 118-134 (1996).
Algarra et al., *Int. J. Clin. Lab. Res.*, 27, 95-102 (1997) (Abstract only).
Antoinia et al., *Int. Immunol.*, 7, 715-725 (1995).
Apostolopoulos et al., *Nat. Med.*, 4, 315-320 (1998).
Berzofsky et al., *J. Clin. Invest.*, 113, 1515-1525 (2004).
Bodey et al., *Anticancer Res.*, 20, 2665-2676 (2000).
Bos et al., *Cancer Res.*, 49, 4682-4689 (1989).
Bos et al., *Mutation Res.*, 195, 255-271 (1988).
Capon et al., *Nature*, 304 (11), 507-513 (1983).
Carbone et al., *J. Clin. Oncol.*, 23, 5099-5107 (2005).
Carbone et al., *Pros. ASCO*, 14, 546 (1995).
Carter et al., *Oncogene*, 5 (3), 411-416 (1990).
Dean et al., *Nat. Rev. Cancer*, 5, 275-284 (2005).
Dudley et al., *Nat. Rev. Cancer*, 3, 666-675 (2003).
Dudley et al., *Science*, 298, 850-854 (2002).
Eishenlohr et al., *J. Immunol. Meth.*, 154, 131 (1992).
Emens et al., *Cancer Res.*, 65, 8059-8064 (2005).
Fenton et al., *J. Nat. Can. Inst.*, 87 (24), 1853-1861 (1995).
Fenton et al., *J. Nat. Can. Inst.*, 85 (16), 1294-1302 (1993).
Fossum et al., *Cancer Immunol. Immunotherapy*, 40, 165-162 (1995).
Fossum et al., *Eur. J. Immunol.*, 23, 2687-2691 (1993).
Fossum et al., *Int. J. Cancer*, 56, 40-45 (1994).
Gaudernack et al., *Immunotech.*, 2, 3-9 (1996).
Gedde-Dahl, *Eur. J. Immunol.*, 23 (3), 754-760 (1993).
Geddle-Dahl et al., *Human Immunol.*, 33, 266-274 (1992).
Gilboa, *Nat. Rev. Cancer*, 4, 401-411 (2004).
Gjertsen et al., *Int. J. Cancer*, 65 (4), 450-453 (1996).
Green et al., *Eur. J. Immunol.*, 34, 2510-2519 (2004).
Hamer et al., *Oncogene*, 6 (9), 1609-1615 (1991).
Hobeika et al., *Crit. Rev. Immunol.*, 21, 287-297 (2001).
Jager et al., *PNAS*, 97, 12198-12203 (2000).
Jung et al., *J. Exp. Med.*, 163, 273-276 (1991).
Juretic et al., *Int. J. Cancer*, 68, 471-478 (1996).
Khan et al., *Oncogene*, 6 (6), 1079-1083 (1991).

(Continued)

*Primary Examiner* — Karen Canella
(74) *Attorney, Agent, or Firm* — Leydig, Voit & Mayer, Ltd.

(57) ABSTRACT

Mutant ras oncogene peptides may induce specific anti-ras cellular immune responses in vaccinated patients. Moreover, a human CD8⁺ CTL epitope(s) reflecting a specific point mutation in the K-ras oncogene at codon 12 was identified. The mutant ras peptide has implications for both active and passive immunotherapies in selected carcinoma patients. A nested 10-mer peptide was identified [i.e., ras5-14(Asp12)], which was shown to bind to HLA-A2 and display specific functional capacity for expansion of the in vivo-primed CD8⁺ CTL precursors.

2 Claims, 11 Drawing Sheets

(56) References Cited

OTHER PUBLICATIONS

Khleif et al., *J. Immunotherapy*, 22 (2), 155-165 (1999).
Khleif et al., *Proc. Amer. Assoc. Can. Res.*, 37 (1996) (Abstract entitled "Induction of T cell responses after vaccination with specific *Ras* mutant peptides in cancer patients").
Kiaris et al., *Int. J. Oncol.*, 7, 413-421 (1995).
Lauritzsen et al., *Int. J. Cancer.*, 78, 216-222 (1998).
Linard et al., *J. Immunol.*, 168, 4802-4808 (2002).
Mitsudomi et al., *Cancer Res.*, 51, 4999-5002 (1991).
Mitsudomi et al., *Oncogene*, 7 (1), 171-180 (1992).
Nagata et al., *Cancer Cell.*, 6, 117-127 (2004).
Ohlen et al., *J. Immunol.*, 166, 2863-2870 (2001).
Paul, *Fundamental Immunology*, 1163-1169 (1993).
Peace et al., *J. Immunol.*, 146, 2059-2065 (1991).
Qin et al., *Cancer Res.*, 55, 2984-2987 (1995).
Rock et al., *PNAS*, 89, 8918-8922 (1992).
Rotzschke et al., *Nature*, 348, 252-254 (1990).
Ruppert et al., *Cell*, 74 (5), 929-937 (1993).
Salter et al., *EMBO J.*, 5, 943-949 (1986).
Semino et al., *J. Biol. Reg. Homeostatic Agents*, 7, 99-105 (1993) (Abstract only).
Skipper et al., *J. Exp. Med.*, 177 (5), 1493-1498 (1993).
Takahashi et al., *Science*, 246, 118-121 (1989).
Thiede et al. *Nucleic Acids Research*, 24, 983-984 (1996).
Tsang et al., *J. Natl. Can. Inst.*, 87 (13), 982-990 (1995).
Tsang et al., *Vaccine Res.*, 3 (4), 183-193 (1994).
Van Bleek et al., *Nature*, 348, 213-216 (1990).
Van Elsas et al., *Int. J. Cancer*, 61 (3), 389-396 (1995).

\* cited by examiner

US 8,883,448 B2

MUTATED RAS PEPTIDES FOR GENERATION OF CD8+ CYTOTOXIC T LYMPHOCYTES

CROSS-REFERENCE TO RELATED APPLICATIONS

This patent application is a continuation of copending U.S. patent application Ser. No. 09/155,590, filed Sep. 30, 1998, which is the U.S. national phase of PCT/US97/06470, filed Apr. 17, 1997, which is a continuation-in-part of U.S. patent application Ser. No. 08/635,344, filed Apr. 19, 1996, and now abandoned, all of which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,761 Byte ASCII (Text) file named "705556_ST25.TXT," created on Nov. 12, 2009.

FIELD OF THE INVENTION

The present invention relates to mutated ras peptides and their use in the generation of human antigen specific cytotoxic T lymphocytes for prevention or treatment of cancer.

BACKGROUND OF THE INVENTION

Cancers in humans are commonly associated with mutations in dominant and recessive oncogenes. These genes produce mutated proteins that are unique to cancer cells. Ras proto-oncogenes are the best characterized mutated genes in human cancer (22-26). They encode a highly conserved family of 21 Kd proteins (p21). With a single amino acid mutation, the ras protein can potentiate transforming capabilities both in mouse and human cells. Such point mutated ras have been found in a broad spectrum of human carcinomas notably at codons 12, 13 and 61. Codon 12 mutations form more than 90% of all ras mutations in human cancers.

Point mutations in the ras p21 proto-oncogenes (i.e., K-ras, H-ras, N-ras) have been identified, described and associated with a high frequency and spectrum of human cancers, including adenocarcinomas of the pancreas, colon and lung as well as melanomas and myeloid leukemias (reviewed in References 1-4). Such mutations lead to the production of aberrant proteins, which are distinct from normal endogenous ras p21 in both structure (DNA and protein sequences) and function and represent early events in cellular transformation. In human carcinomas which harbor p21 point mutations, it is the K-ras gene at codon 12 that is found frequently mutated, whereby the normal glycine (Gly) residue is replaced with either an aspartic acid (Asp), valine (Val), cysteine (Cys), alanine (Ala), arginine (Arg) or serine (Ser) residue (1,2,4). Substitutions of Gly to Asp, Val and Cys, collectively, however, account for the majority of human carcinomas with such p21 position 12 point mutations (1,2,4).

T Lymphocytes can recognize antigens (Ag) presented in the context of major histocompatibility complex (MHC) class I or class II molecules on the surface of antigen presenting cells (APC) (27-31). These surface Ag are thought to be short peptides that are derived from degraded intact proteins (32-34).

T lymphocytes are divided into two major populations, CD4+ and CD8+. The CD8+ T cells recognize peptides (8-10 residues) bound to MHC class I molecules and are associated with cytotoxic activity (30-31). The CD4+ lymphocytes are generally involved in the recognition of peptides (13-18 residues) presented in the context of MHC class II molecules (28,29), and are involved in immunoregulation through cytokine secretion. Th1, a subset of CD4+ T cells have been reported to express lytic activity (35-37).

Data in mice has shown the generation of MHC restricted (specific) cytotoxic T cells that are capable of detecting endogenous, cytoplasmic peptide antigens (antigens presented from within the cell membrane on the cell surface)[38,39]. These T cells can cause rejection (lysis) of cells expressing such peptides. This rejection is mediated by cells responding to novel peptides derived from mutated genes (38,39). T cells are capable of detecting single amino acid discrepancies between homologous peptides presented on APC (40,41).

The generation and expression of these previously unseen, "neo-determinants" may now represent unique and highly specific epitopes for T cell (CD4+ and/or CD8+) recognition, which has been proposed in host defense as an important effector pathway in the control of malignancy (5). Studies in both murine and human systems, have previously identified and characterized immunodominant CD4+ T cell epitopes of mutant K-ras at codon 12 using short synthetic peptides (6-12). With respect to human anti-ras CD8+ cytotoxic T lymphocyte (CTL) responses, however, nothing is yet defined for position 12 mutations, although one has been reported for position 13 and one for position 61 (13, 14). Thus, the identification herein of human CD8+ T cell epitopes reflecting specific ras p21 point mutations has important and direct implications for the development of oncogene-specific vaccines in cancer immunotherapy.

SUMMARY OF THE INVENTION

The invention is mutant ras peptides and variants or analogs thereof which elicit antigen specific cytotoxic T lymphocytes. The mutant ras peptides are T cell epitopes for CD8+ human T lymphocytes.

Another aspect of the invention is a pharmaceutical composition comprising one or more mutant ras peptides and a pharmaceutically acceptable carrier. The pharmaceutical composition is useful as an immunogen and as a therapeutic in the prevention or treatment of cancer and in inhibiting growth of tumors expressing a ras mutation. The pharmaceutical composition may further comprise an adjuvant or a liposome formulation.

Another pharmaceutical composition comprises a mutant ras peptide-pulsed antigen presenting cell and a pharmaceutically acceptable carrier. The composition is useful as an immunogen and as a therapeutic.

A further object of the invention is a mutant ras p21 protein or peptide specific cytotoxic T lymphocyte which prevents the occurrence of tumor cells and inhibits the growth of or kills tumor cells which express the mutant ras p21 protein or peptide.

Another aspect of the invention is a method of generating cytotoxic T lymphocytes specific against tumors expressing a ras mutation by in vivo administration of an effective amount of at least one mutant ras peptide alone, or in combination with an adjuvant, in a liposome formulation, or by administration of mutant ras peptide-pulsed antigen presenting cells. The antigen specific cytotoxic T lymphocytes which arise from immunization are useful in methods of inhibiting or killing tumor cells expressing a mutant ras p21 protein or peptide.

Yet another aspect of the invention is a method of generating cytotoxic T lymphocytes specific against tumors expressing a ras mutation in vitro by stimulation of lymphocytes from a source with an effective amount of a mutant ras peptide, alone or in combination with one or more cytokines. Such antigen specific cytotoxic T lymphocytes may be adoptively transferred into a mammal for the prevention or treatment of cancer and to inhibit or kill tumors expressing the mutant ras protein, or peptide. Further, the cytotoxic T lymphocytes are useful in methods for screening for antigen epitope mapping.

A further aspect of the invention is a method of preventing the occurrence, inhibiting the growth of or killing tumor cells expressing mutant ras p21 protein or peptides comprising a) generating mutant ras protein or peptide specific cytotoxic T lymphocytes in vitro by stimulation of lymphocytes from a source with an effective amount of a mutant ras peptide, alone or in combination with one or more cytokines, the amount being effective in generating mutant ras protein or peptide specific cytotoxic T lymphocytes, and b) adoptively transferring the mutant ras protein or peptide specific cytotoxic T lymphocytes alone, or in combination with one or more cytokines into a mammal in an amount sufficient to prevent the occurrence of, inhibit the growth of, or kill the tumor cells.

Another aspect of the invention is a method of preventing the occurrence, inhibiting the growth or killing tumor cells expressing mutant ras p21 protein or peptide in a mammal comprising a) generating mutant ras p21 protein or peptide specific cytotoxic T lymphocytes in vivo by administration of an effective amount of a mutant ras protein alone, or in combination with an adjuvant or as a liposome formulation, and b) the mutant ras p21 protein or peptide specific cytotoxic T lymphocytes so generated prevent the occurrence of, inhibit the growth of, or kill the tumor cells in the mammal.

Another object of the invention is a DNA sequence encoding one or more mutant ras peptides.

Another object of the invention is a vector comprising at least one insertion site containing a DNA sequence encoding one or more mutant ras peptides, operably linked to a promoter capable of expression in a host cell.

Yet another object of the invention is a method of generating mutant ras peptide specific cytotoxic T lymphocytes by administration into a mammalian host an effective amount of a recombinant virus vector comprising at least one insertion site containing a DNA sequence encoding a mutant ras peptide.

DESCRIPTION OF THE DRAWINGS

(FIG. 1A) Proliferative response measured weekly starting at IVS cycle 3; and (FIG. 1B) Proliferative response at IVS cycle 6 against specific and irrelevant peptides. Phenotypic analysis revealed the T cell culture>85% $CD4^+$.

(FIG. 2A) MAb directed against HLA class I (i.e., anti-HLA-A,B,C) or class II (i.e., anti-HLA-DR, DP or DQ) molecules were used to define the role and importance of MHC restriction for T cell activation. The T cell line of RAS patient 43 was assayed after IVS cycle 10 using autologous BLCL as APC, incubated with peptide (10 µg/ml) ±MAb at different concentrations. Results are expressed as % control, as defined by the equation: [(activity with $MAb_{cpm}$–$control_{cpm}$)/(activity without $MAb_{cpm}$–$control_{cpm}$)]×100, where $control_{cpm}$ refers to unstimulated cultures of T cells+ BLCL without peptide). (FIG. 2B) In a separate experiment, MAb directed against the CD4 (clone OKT4; hybridoma supernatant, 20% v/v) or CD8 (clone OKT8; hybridoma supernatant, 20% v/v) molecules were used to identify and confirm the functional T cell subset(s). Also included in this assay were MAb directed against HLA class I or II molecules (each at 3 µg/ml), as in FIG. 2A. In FIG. 2B, the T cell line was tested after IVS cycle 15 using autologous BLCL as APC, incubated with Cys12 peptide (10 µg/ml)±MAb. Additional control cultures (cpm±SEM) included: irradiated BLCL, 8,520±225; T cells+BLCL+Gly12 peptide (10 µg/ml), 7,690±383).

FIG. 8A: Unfractionated PBMC, pre-vaccination and post-third vaccination, were stimulated biweekly using autologous PBMC as APC incubated with mutant ras 13-mer peptide [i.e., ras5-17(Val12)] and IL-2, similar to patient 43 (see Table 3). PBMC cultures were following the second IVS. Proliferation was measured by $^3$H-thymidine uptake and the results were expressed as stimulation index (SI). FIG. 8B: MAb directed against the CD4 (clone OKT4; hybridoma supernatant, 20% v/v) or CD8 (clone OKT8; hybridoma supernatant, 20% v/v) molecules were used to identify and confirm the functional T cell subset(s). The T cell line of patient 29 was assayed after IVS cycle 4 using autologous EBV-B cells as APC, incubated with ras5-17(Val12) peptide (3 µg/ml) MAb. Additional control cultures (cpm±SEM) included: irradiated EBV-B cells (3,535±372); T cells+EBV-B cells (19,256±1926); T cells+EBV-B cells+Gly12 peptide (3 µg/ml), (18,116±1474).

FIG. 9A: A CD8+ CTL line was established from post-vaccinated PBMC of patient 29 and assayed for peptide specificity against C1R-A2 targets. Cytotoxicity was determined by $^{51}$Cr-release, and the results expressed at different effector/target ratios following IVS cycle 7. FIG. 9B: Using this CD8+ CTL line, the requirement for HLA-A2 in peptide presentation (by autologous EBV-B cells as targets) was determined in blocking experiments using MAb (clone BB7.2; ascites=1:30 dilution) directed against that molecule (or using an isotype-matched MAb). IVS cycle=11; effector/target ratio=10/1; ras5-14(Val12) peptide=3 µg/ml. CD4 and CD8 MAbs were as described for FIGS. 8A and 8b. Control lysis in the absence of peptide or in the presence of ras5-14(Gly12) was <3%.

FIG. 10A: Anti-ras Val12-specific CD8+ CTL from patient 29 were assayed against the SW480 colon carcinoma cell line (HLA-A2+, rasVal12+) in the absence of exogenous peptide, with or without IFN-γ pretreatment (250 U/ml for 24 hr) of the target cells. CD8+ CTL reactive with the MART-1$_{25-27}$ peptide were used as an irrelevant effector cell population. Cytotoxicity was determined by $^{51}$Cr-release, and the results expressed at different effector/target ratios. FIG. 10B: In parallel to 10A, anti-ras or anti-MART-1-specific CTL were assayed against SW480 (±IFN-γ pretreatment) at an effector/target ratio of 10/1 in the absence or presence of exogenous peptide (5 µg/ml). For anti-ras CTL: specific peptide=ras5-14(Val12); control peptide=ras5-14 (Gly12). For anti-MART-1 CTL: specific peptide=MART-1$_{27-35}$; control peptide=ras5-14(Val12). Flow cytometric analysis of SW480 cells for expression of HLA-A2: untreated=65.4% with MFI of 29.8; IFN-γ-pretreated=99.5% with MFI of 349.6. Flow cytometric analysis of SW480 cells for expression of ICAM-1: untreated=16.0% with MFI of 30.3; IFN-γ-pretreated=98.6% with MFI of 181.9.

DETAILED DESCRIPTION OF THE INVENTION

Figure 1A:
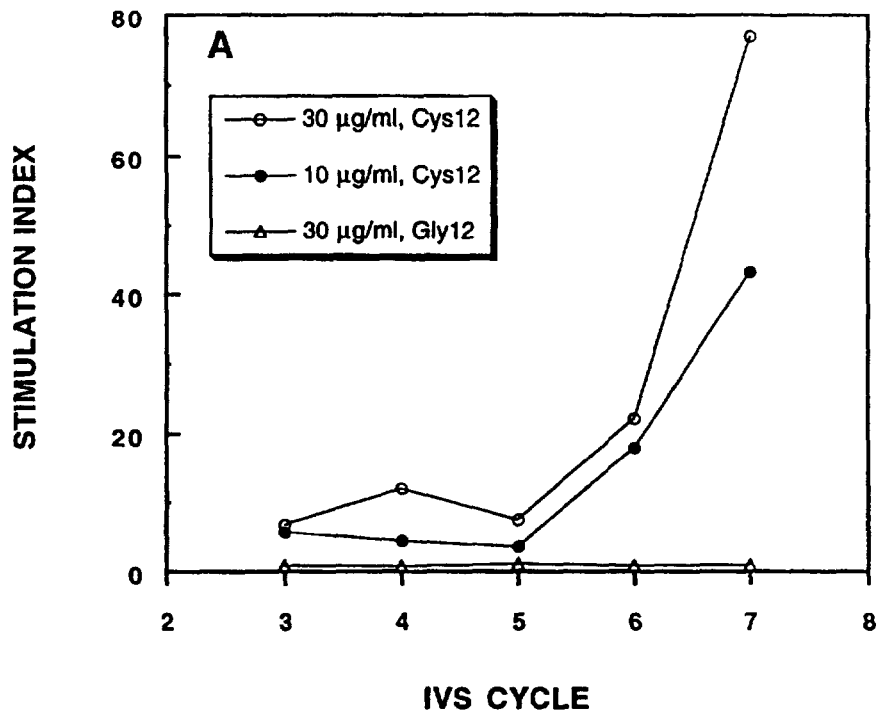
FIGS. 1A and 1B. Generation of a peptide-specific $CD4^+$ T cell line from immune lymphocytes of RAS patient 43. Following the third vaccination, a $CD4^+$ T cell line from RAS patient 43 was established and maintained in culture by continuous weekly IVS of unfractionated immune lymphocytes with autologous PBMC (up to cycle 3) or BLCL (thereafter) as APC incubated with the mutant ras 13-mer peptide and IL-2. Demonstration of Ag specificity and potency of the T cell culture was examined by lymphoproliferation, and the results expressed as stimulation index.

The invention is a mutated ras peptide, analog or variant thereof. The mutated ras peptide is characterized by its ability to elicit an immune response specific against mutant ras-p21 protein or portion thereof and against cells expressing or binding mutant ras-p21 protein or portion thereof.

The mutant ras peptide of the present invention elicits antigen specific cytotoxic T lymphocytes which inhibit the growth or kill cells expressing mutant ras-p21 protein or peptides thereof.

Cells that express mutant ras-p21 protein or peptides thereof include but are not limited to cancer cells, in particular, human cancer cells. Such cancers include, but are not limited to, adenocarcinomas of the pancreas, colon, endometrial, lung, thyroid, melanoma, oral laryngeal, seminoma, hepatocellular, bile duct, acute myeloblastic leukemia, basal cell carcinoma, squamous cell carcinoma and the like.

Of particular interest are cancers with position 12 mutations in the ras p21 protein or peptide.

Three ras genes with transforming potential include H-, K- and N-ras. H-, K- and N-ras p21 proteins share an overall 75% amino acid homology. Within the N-terminal catalytic domains (positions 5 to 120) the homology between the three oncogenes is greater than 97%. Thus, the pointed mutated ras peptides of the present invention are effective in treating cancers induced by one or more ras oncogenes. Such cells expressing mutant ras-p21 protein or peptides may be inhibited from growing or killed by mutant ras-p21 peptide specific cytotoxic T lymphocytes or CD8+ lymphocytes, both in vitro and in vivo.

The mutant ras peptides of the present invention comprises between about 8-13 amino acids, preferably about 9-10 amino acids. The mutated ras peptides of the invention comprise one point mutation each as compared to normal endogenous ras p21 protein.

In one embodiment, the mutant ras peptide or portion thereof comprises a point mutation at amino acid position 12 as compared to normal ras-p21. In another embodiment, the mutated ras-peptide comprises about 10 amino acids and contains a point mutation at amino acid position 12.

The mutant ras-peptide comprises a peptide whereby normal glycine at position 12 is replaced with an amino acid selected from the group consisting of: aspartic acid, valine, cysteine, alanine, arginine and serine. In a preferred embodiment, the mutant ras-peptide comprises a substitution of glycine at 12 with an amino acid selected from the group consisting of aspartic acid, valine and cysteine.

In one embodiment, the mutant ras peptide or portion thereof comprises the following amino acid sequence:

Amino Acid and Position

```
ras Peptides      4 5 6 7 8 9 10 11 12 13 14 15 16 17

(SEQ. ID NO. 1)
Normal  ras5-17   Lys-Leu-Val-Val-Val-Gly-Ala-Gly-Gly-
(Gly 12)          Val-Gly-Lys-Ser (SEQ. ID NO. 2)
Mutant  ras5-17   Lys-Leu-Val-Val-Val-Gly-Ala-Asp-Gly-
(Asp12)           Val-Gly-Lys-Ser (SEQ. ID NO. 3)
Mutant  ras5-14   Lys-Leu-Val-Val-Val-Gly-Ala-Asp-Gly-
(Asp12)           Val (SEQ. ID NO. 4)
Mutant  ras5-14   Lys-Leu-Val-Val-Val-Gly-Ala-Val-Gly-
(Val12)           Val (SEQ. ID NO. 5)
Mutant  ras5-14   Lys-Leu-Val-Val-Val-Gly-Ala-Cys-Gly-
(Cys12)           Val (SEQ. ID NO. 6)
Mutant  ras4-12   Tyr-Lys-Leu-Val-Val-Val-Gly-Ala-Val
(Val12)
``` or variants or analogs thereof. Variants or analogs may be constructed that elicit a more potent T-cell response.

Analogs are constructed for enhanced binding to MHC class I molecules and/or enhanced binding to the T cell receptor for an improved immune response. Variants or analogs may include but are not limited to peptides having a single amino acid substitution at a position distinct from position 12. Such substitutions include but are not limited to changing Lys at position 5 with Tyr. In one such embodiment, a variant of SEQ ID NO.: 3 includes Tyr-Leu-Val-Val-Val-Gly-Ala-Asp-Gly-Val (SEQ. ID NO.: 11).

The mutant ras peptide may be obtained by recombinant DNA technology, by chemical peptide synthesis or by appropriate protease cleavage of an isolated, mutant ras protein or peptide.

The mutant ras peptide may be formulated into a pharmaceutical composition in combination with a pharmaceutically acceptable carrier for use as an immunogen in a mammal, preferably a human. The composition may further comprise one or more other constituents to enhance the immune response which include but are not limited to biological response modifiers such as interleukin 2, interleukin 6, interleukin 12, interferon, tumor necrosis factor, GM-CSF, and cyclophosphamide.

The mutant ras peptide is administered to a mammal in an amount effective in generating a mutant ras peptide specific immune response, preferably a cellular immune response. The efficacy of the mutant ras peptide as an immunogen may be determined by in vivo or in vitro parameters as are known in the art. These parameters include but are not limited to antigen specific cytotoxicity assays, regression of Ras-p21$^+$ tumors, inhibition of Ras-p21$^+$ cancer cells, production of cytokines and the like.

At least one or more mutant ras peptides may be administered in a dose of about 0.05 mg to about 10 mg per vaccination of the mammal, preferably about 0.1 mg to about 5 mg per vaccination. Several doses may be provided over a period of weeks as indicated. In one embodiment a dose is provided every month for 3 months. The mutant ras peptide may be administered alone or in combination with adjuvants, in a liposome formulation, cytokines, biological response modifiers, or other reagents in the art that are known to enhance immune response. Adjuvants include but are not limited to RIBI Detox™, QS21, alum and incomplete Freund's adjuvant. In one embodiment, the mutant ras peptide is administered in combination with Detox™ (RIBI Immunochem, Hamilton, Mont.).

The mutant ras peptides may also be conjugated to helper peptides or to large carrier molecules to enhance the immunogenicity of the peptide. These molecules include but are not limited to influenza peptide, tetanus toxoid, tetanus toxoid CD4 epitope, *Pseudomonas* exotoxin A, poly-L-lysine, and the like.

Another effective form of the mutant ras peptide for generating a mutant ras peptide specific immune response in a mammal is a mutant ras peptide-pulsed antigen presenting cell. The antigen presenting cells include but is not limited to dendritic cells, B lymphocytes, monocytes, macrophages and the like. In a preferred embodiment, the mutant ras peptide-pulsed antigen presenting cell is a dendritic cell.

The invention also provides a method of generating mutant ras peptide specific cytotoxic T lymphocytes in vivo or in vitro by stimulation of lymphocytes from a source with an effective amount of a mutant ras peptide alone or in combination with a biological response modifier and/or adjuvant or in a liposome formulation. The sources of lymphocytes include but are not limited to peripheral blood, tumor tissues, lymph nodes and effusions such as pleural fluid or ascites fluid and the like.

The mutant ras p21 protein or peptide specific cytotoxic T lymphocytes of the present invention are immunoreactive with mutant ras p21 protein or peptide. The cytotoxic T lymphocytes inhibit the occurrence of tumor cells and cancer and inhibit the growth or kill mutant ras p21 protein or peptide expressing tumor cells. The cytotoxic T lymphocytes, in addition to being antigen specific, are MHC class I restricted. In one embodiment the cytotoxic T lymphocytes are MHC class I HLA-A2 restricted. The cytotoxic T lymphocytes have a CD8$^+$ phenotype. The cytotoxic T lymphocytes may be restricted by other HLA alleles including but not limited to A3, A11, A68, A24 and the like.

A peptide-based, phase I clinical trial was initiated in metastatic carcinoma patients whose tumors contain point mutations in the ras p21 proto-oncogenes at codon 12. The majority of patients in this study presented primary malignancies of the colon, GI tract, lung and pancreas and harboring position 12 mutations of Gly to Asp, Cys or Val.

Selected patients were vaccinated subcutaneously up to three times at monthly intervals with DETOX™ adjuvant admixed with the appropriate mutated ras 13-mer peptide spanning positions 5-17, which corresponded to the specific point mutation at codon 12 found in their cancer. Recently, Gjertsen et al. (15) reported on the vaccination of pancreatic carcinoma patients with autologous peripheral blood mononuclear cells pre-pulsed ex vivo with mutant ras peptides (spanning positions 5-21) reflecting codon 12 mutations. Of five patients receiving multiple vaccinations, two patients showed evidence of anti-ras T cell responses, as measured by proliferation assays. In one patient, the T cell response was specific for the immunizing peptide (Val12); whereas, in the other patient, the T cell response cross-reacted with both immunizing (Asp12) and non-mutated (Gly12) peptides. In both patients, these responses were transient in that they were detectable at day 40 after the onset of vaccination, but undetectable during the following weeks. No other phenotypic or functional studies were reported.

In the present invention, the capacity to induce peptide-specific cellular immune responses in patients vaccinated with mutant ras peptides was shown. Moreover, the present invention provides for the first time of a human HLA-A2-restricted, CD8+ CTL epitope reflecting the codon 12 mutation, Gly to Asp. Major histocompatibility complex (MHC) class II-restricted CD4+ T cell lines were derived from individual patients. In addition, MHC class I-restricted CD8+ T cell line was produced, which recognized a nested sequence of the original immunogen. Both CD4+ and CD8+ T cell lines could be maintained long term in culture without loss of antigen (Ag) specificity. Furthermore, in the patients, no specific T cell responses were found against the normal ras sequence and no T cell lines were generated in culture from pre-immune lymphocytes. Taken collectively, vaccination with oncogene-derived mutant ras peptides of the present invention induces highly specific and systemic anti-ras cellular immune responses. Moreover, the development of such MHC class I-restricted mutant ras peptides has important implications for both active (i.e., vaccination) and passive (i.e., ex vivo expansion for cellular adoptive transfer) immunotherapies, which may be used for the induction and propagation of specific CD8+ CTL responses in cancer patients.

In accordance with the present invention, patient immune status was compared pre-vaccination and postthird vaccination. The phenotypic and functional properties of the resulting T cell lines established from those patients which displayed evidence of cell-mediated immunity were characterized. The capacity to induce peptide-specific CD4+ T cell responses in a subset of patients following vaccination with ras oncogene peptides reflecting the corresponding ras mutation was confirmed. Moreover, the present invention provides for the first time the identification of human HLA-A2-restricted, CD8+ CTL epitopes reflecting two distinct codon 12 mutations, which were found to be nested within the longer 13-mer peptide immunogen (i.e., ras5-14(D12)). Thus, in an aspect of the present invention, it was demonstrated that a single mutant ras peptide immunogen contained both CD4+ and CD8+ T cell epitopes in a nested configuration. Experimental models were established in vitro, which demonstrated the capacity of CD4+ and CD8+ T cell lines to recognize antigen presenting cell (APC) populations presenting the corresponding oncoprotein or tumor cells harboring the naturally-occurring mutation.

That a single mutant ras peptide immunogen contains both CD4+ and CD8+ T cell epitopes in an overlapping or nested configuration, as demonstrated by the present invention, affords important biological implications for the generation and coordination of a more efficient anti-pathogen immune response. Similarly, in a murine model, overlapping MHC class II-restricted CD4+ and MHC class Irestricted CD8+ CTL peptide epitopes were also identified, thus reflecting the ras Val12 mutation. In accordance with the present invention, oncogene-specific CD4+ and CD8+ T cell lines may be considered for employment in adoptive immunotherapy, perhaps in concert with active immunization for a more comprehensive antitumor attack. Furthermore, as supported by the present invention, modifications in immunogen design, schedule and delivery, along with the co-administration of cytokines such as IL-2, IL-12 or GM-CSF, are likely to enhance both the development of the immune response and potential clinical benefit.

In accordance with the present invention, methods were developed for improving the sensitivity and consistency for detecting weakly positive peptide-specific proliferative responses and functional evaluation of cultured lymphocyte populations. To this end, patient lymphocyte populations were incubated in vitro (at 7-14 day intervals) with an autologous source of APC, mutant ras peptide as antigen (Ag) and IL-2, and then were retested for peptide-specific reactivity at or toward the end of an IVS cycle. Such culture conditions were developed to reflect the nominal requirements for Ag-specific expansion of in vivo peptide-primed lymphocytes and their subsequent testing as evidence for "recall" responses to vaccination. These IVS cycles were established to: (i) amplify detection of a weak, but specific functional response; (ii) compare pre-vaccine to post-vaccine lymphocytes over a period of time for assessment of potential peptide-specific reactivity; and (iii) derive peptide-specific T cell lines in culture for detailed phenotypic and functional characterization.

According to the present invention, methods for the induction of CD8+ CTL specific for position 12 mutations are provided. HLA-A2-restricted responses were identified in two of three vaccinated patients. This was made possible, in large part, by the initial identification of a nested peptide sequence bearing a consensus anchor motif for HLA-A2, which displayed functional binding to that molecule (Table 7). In vivo priming of the CD8+ T cell response likely resulted from in vitro mechanisms of Ag processing (i.e., extracellular or intracellular), perhaps influenced and potentiated in the presence of adjuvant, with the subsequent generation of MHC class I-reactive epitopes. Although the CTL analysis was initially examined and demonstrated for HLA-A2/peptide interactions, the present invention provides vaccination-induced CTL responses restricted by other HLA class I alleles. Thus, insights into patient immune responsiveness to these immunogens may be provided by a detailed analysis of HLA restriction patterns for peptide presentation, and identification of putative consensus anchor motifs.

Patients with solid tumors expressing mutant ras, including but not limited to colon cancer, lung cancer, pancreas cancer, endometrial cancer, thyroid cancer, melanoma, oral cancer, laryngeal cancer, seminoma, hepatocellular cancer, bile duct cancer, acute myeloblastic leukemia, basal cell carcinoma, squamous cell carcinoma, prostate cancer and the like benefit from immunization with the mutant ras peptides. A tumor tissue sample is obtained from a patient for determination of the ras mutation using techniques known in the art such as PCR analysis. Patients amenable to treatment using the mutant ras peptides of the present invention are those patients having tumors with ras mutations in the normal ras p21 protein. Of particular interest are tumors with a point mutation in codons 12, in particular mutations resulting in Gly to Cys, Gly to Asp, Gly to Val, Gly to Ala, Gly to Arg and Gly to Ser at position 12.

The mutant ras peptide used for immunization is one which corresponds with the ras mutation in the tumor of the patient. The peptides may be chemically synthesized under GMP conditions and purified by HPLC to >95% purity and lyophilized. Pharmaceutical compositions are formulated by reconstituting the peptide with a pharmaceutically acceptable carrier such as sodium chloride. In one example, each milliliter of solution contains 1500 µg of a mutant ras peptide plus 9.0 mg sodium chloride. The mutant ras peptides with Cys or Val at position 12 are formulated at pH=about 4.5 to about 6.5. The mutant ras peptide with Asp at position 12 are formulated at pH=about 3.5 to about 5.5.

When the mutant ras peptide is administered with an adjuvant it is desirable to mix the peptide with the adjuvant shortly before administration to a patient.

The mutant ras peptide may be administered to a patient by various routes including but not limited to subcutaneous, intramuscular, intradermal, intraperitoneal, intravenous and the like. In one embodiment the mutant ras peptide is administered subcutaneously. The peptide may be administered at one or more sites to a patient. In one embodiment, the peptide, alone or in combination with an adjuvant, is administered into three sites subcutaneously, over the deltoids, the thighs and the abdomen.

In another method of generating an immune response, mutant ras peptide-pulsed antigen presenting cells are administered to the patient in an amount effective to generate an antigen specific immune response. The antigen presenting cells include but are not limited to dendritic cells, B lymphocytes, monocytes, macrophages and the like. In one embodiment, dendritic cells are isolated from a patient by methods described in Romani, N. et al (1994). The isolated dendritic cells are cultured in vitro with a mutant ras peptide for a period of about 0.5 to about 3 hours and washed to remove non-bound peptide. The mutant ras peptide-pulsed dendritic cells are transferred back into the patient at a concentration of about $10^6$ to about $10^9$ dendritic cells. Such a concentration is effective in generating an immune response in the patient including the generation of mutant ras p21 protein or peptide specific cytotoxic T lymphocytes which are able to inhibit the growth or kill tumor cells.

The criteria for determining an anti-tumor response in the immunized patient is as follows:

1. Complete Remission (CR): Complete disappearance of all evidence of tumor and return of abnormal tests to normal levels for a minimum of 4 weeks.

2. Partial Response (PR): Decrease by at least 50% in the sum of the products of the perpendicular diameters of all measured lesions in the absence of progression of any lesion nor the appearance of any new lesions for at least 4 weeks.

3. Stable Disease (SD): Change in measurable disease two small to meet the requirements for partial response or progression and the appearance of no new lesions for a period of at least 12 weeks. There may be no worsening of symptoms.

4. Progressive Disease (PD) or Relapse: Any one of the criteria below must be met to be considered progressive disease:

Development of any new area of malignant disease (measurable or palpable),

Increase (>25%) in any pretreatment area of measurable malignant disease.

The immunological response to immunization with the mutant ras peptides are assessed by in-vitro T cell proliferation assay and/or by in-vitro T cell cytotoxic assay before and after vaccination.

In Vitro T Cell Proliferation Assay:

The patient PBMC are incubated in vitro with the appropriate tumor specific ras peptide, and evaluated for peptide-induced proliferation following up to 6 days of incubation. Cultures are pulsed with [$^3$H]-thymidine for the final 18-24 hours of their culture. Proliferation is measured and quantified by the incorporation of [$^3$H]-thymidine. A proliferation of more than three fold above control (i.e. without peptide stimulation or with the normal ras peptide) is considered as a positive response.

In Vitro T Cell Cytotoxic Assay:

The T cell cytotoxicity is measured by the standard [$^{51}$Cr]-release assay. Briefly, target cells (autologous tumor cells or autologous EBV-transformed B cells) are radiolabeled with $Na_2{}^{51}CrO_4$. The patient PBMC (which has previously stimulated with the appropriate ras peptide) is added to the labeled target cells in the presence or absence of the corresponding ras peptide. Cell lysis is determined by the specific release of $^{51}$Cr (specific lysis). If there is a detectable pre-immunization specific lysis, a 1.5 fold increase in the lysis will be considered a positive response. If there is no detectable pre-immunization specific lysis, a post-immunization specific lysis of than 15% is considered a positive response.

The present invention includes in vitro immunization for T cell proliferation and generation of cytotoxic T cell lines to the tumor specific ras mutated peptide. In vitro cultivation of peptide specific T cells from peripheral blood mononuclear cells (PBMC), lymph node tissue (LNT), or tumor infiltrating lymphocytes (TIL) with mutant ras peptide and IL2 generates peptide specific T cells. These T cells are tested for cytotoxicity against mutant ras peptide primed APC (autologous EBV transformed B cells or autologous tumor cells) has described herein. Generated T cell clones are characterized phenotypically by flow cytometry for express of CD3, CD4, and CD8. Mutant ras peptide specific cytotoxic lymphocytes may be adoptively transferred to a patient in order to inhibit or kill mutant ras p21 expressing tumor cells. Patients may then be reimmunized with mutant ras peptide preferably in adjuvant.

Generally, between about $1\times10^5$ and $2\times10^{11}$ cytotoxic T cells per infusion are administered in, for example, one to three infusions of about 200 to about 250 ml each over a period of 30 to 60 minutes. After completion of the infusions, the patient may be treated with a biological response modifier such as interleukin 2 (IL-2). In the case of IL-2, recombinant IL-2 is administered intravenously in a dose of 720,000 IU per kilogram of body weight every eight hours. After adoptive transfer of the antigen specific cytotoxic T cells into the patient, the patient may be additionally treated with the mutant ras peptide used to prime the cytotoxic T cells, to further expand the T cell number in vivo.

The invention encompasses a DNA sequence and analogs thereof which encode a mutant ras peptide. The DNA sequence encoding the mutant ras peptide differs from the DNA sequence of the normal ras p21 protein or peptide by a point mutation in the DNA sequence. Of particular interest are DNA sequences comprising a point mutation at the codon encoding the amino acid at position 12. The normal codon encoding glycine at position 12, i.e. GGT, may be substituted by a mutant codon encoding aspartic acid, cysteine, valine, alanine, arginine, and serine. In a preferred embodiment, the normal codon is substituted by a mutant codon encoding aspartic acid, valine, or cysteine.

In one embodiment the DNA sequence encoding the mutant ras peptide comprises:

```
TAT AAA CTT GTG GTA GTT GGA      (SEQ. ID NO. 7)
Tyr Lys Leu Val Val Val Gly      (SEQ. ID NO. 12)
 5                       10

GCT GAT GGC GTA GGC AAG AGT
Ala Asp Gly Val Gly Lys Ser
                15
``` or portion or variant thereof.

In another embodiment the DNA sequence encoding the mutant ras peptide comprises:

```
TAT AAA CTT GTG GTA GTT GGA      (SEQ. ID NO. 8)
Tyr Lys Leu Val Val Val Gly      (SEQ. ID NO. 13)
                         10

GCT TGT GGC GTA GGC AAG AGT
Ala Cys Gly Val Gly Lys Ser
                15
``` or portion or variant thereof.

In yet another embodiment, the DNA sequence encoding the mutant ras peptide comprises:

```
TAT AAA CTT GTG GTA GTT GGA    (SEQ. ID NO. 9)
Tyr Lys Leu Val Val Val Gly    (SEQ. ID NO. 10)
 5                      10

GCT GTT GGC GTA GGC AAG AGT
Ala Val Gly Val Gly Lys Ser
                 15
``` or portion or variant thereof.

The present invention encompasses conservative substitutions based on codon degeneracy, provided that the modification results in a functionally equivalent mutant ras peptide or a peptide with enhanced immunogenicity. Included are substitutions in codons in positions distinct from the codon encoding the amino acid at position 12. For example, the codon which encodes the amino acid lysine at position 5 may be replaced by the codon encoding tyrosine.

The invention further provides vectors and plasmids comprising a DNA sequence encoding a mutant ras peptide. The vectors include but are not limited to E. coli plasmid, a Listeria vector and recombinant in vector. Recombinant viral vectors including but not limited to orthopox virus, avipox virus, capripox virus, suipox virus, vaccinia, baculovirus, human adenovirus, SV40, bovine papilloma virus, and the like comprising the DNA sequence encoding a mutant ras peptide.

Recombinant mutant ras peptide can be obtained using a baculovirus expression system in accordance with the method of Bei et al J. Clin. Lab. Anal. 9:261-268 (1995). Recombinant viral vectors can be constructed by methods known in the art such as U.S. Pat. No. 5,093,258; Cepko et al Cell 37:1053-1062 (1984); Morin et al Proc. Natl. Acad. Sci. USA 84:4626-4630 (1987); Lowe et al Proc. Natl. Acad. Sci. USA 84:3896-3900 (1987); Panicali & Paoletti, Proc. Natl. Acad. Sci. USA 79:4927-4931 (1982); Mackett et al, Proc. Natl. Acad. Sci. USA 79:7415-7419 (1982); WO 91/19803; Perkus et al Science 229:981-984 (1985); Kaufman et al Int. J. Cancer 48:900-907 (1991); Moss Science 252:1662 (1991); Smith and Moss BioTechniques November/December, p. 306-312 (1984); U.S. Pat. No. 4,738,846; Sutter and Moss Proc. Natl. Acad. Sci. USA 89:10847-10851 (1992); Sutter et al Virology (1994); and Baxby and Paoletti Vaccine 10:8-9 (1992).

Host cells which may express the DNA encoding the mutant ras peptide carried by vectors or plasmids are prokaryotic and eukaryotic host cells and include but are not limited to E. coli, Listeria, Bacillus species, COS cells, Vero cells, chick embryo, fibroblasts, tumor cells, antigen presenting cells and the like. When the host cell is an antigen presenting cell, the host cell is an antigen presenting cell, the host cell should additionally express an MHC class I molecule.

The invention has been described in detail including the preferred embodiments thereof. However, it will be appreciated by those skilled in the art, upon consideration of this disclosure, may make modifications and improvements thereon without departing from the spirit and scope of the invention as set forth in the claims.

Reference and patents referred to are incorporated herein by reference.

EXAMPLES

Example 1

Materials and Methods

Patient selection.

adult cancer patients with histologically confirmed diagnosis of adenocarcinoma of the colon, gastrointestinal tract, lung or pancreas with metastatic disease, were screened as potential candidates for this phase I clinical study. Tumor samples from these patients were examined for point mutations in the K-ras gene at codon 12 by polymerase chain reaction (PCR) of paraffin-embedded sections by methods known in the art. In addition to fulfilling all other essential inclusion criteria as specified in the FDA-approved NCI clinical protocol, those patients presenting the appropriate K-ras mutation were then selected for study entry.

Peptides and Immunizations.

Mutant ras 13-mer peptides used as immunogens were synthesized as clinical grade reagents under GMP conditions (Bachem, Torrance, Calif.: >97% purity by HPLC). Control and additional experimental peptides, which were used in vitro, either were prepared commercially (Bachem) or synthesized in the laboratory on an Applied Biosystems Model 432A personal peptide synthesizer (Foster City, Calif.) using Fmoc chemistry (>90% purity by HPLC). These reagent-grade products were dissolved in aqueous solution at 2 mg/ml, filter-sterilized and stored in aliquots at −70° C. The normal sequence of ras p21 reflecting positions 5-17 is Lys-Leu-Val-Val-Val-Gly-Ala-<u>Gly</u>-Gly-Val-Gly-Lys-Ser (KLV-VVGA<u>G</u>GVGKS) (SEQ. ID NO. 1). The mutant ras 13-mer peptides used as immunogens in this study reflected the substitution of <u>Gly</u> at position 12 with either an <u>Asp</u>, <u>Cys</u> or <u>Val</u> residue. Patients were injected subcutaneously (s.c.) at multiple sites (i.e. deltoid, thigh and abdomen) with the appropriate mutant ras 13-mer peptide corresponding to the specific point mutation previously identified in an autochthonous tumor sample. Prior to each vaccination, the peptide was prepared freshly from a lyophilized stock, reconstituted in sterile water, and admixed by vortexing with clinical grade Detox™ adjuvant (RIBI ImmunoChem Research, Hamilton, Mont.) as described by the manufacturer. The Detox™ adjuvant, supplied in a lyophilized form, was composed of two active immunostimulants: cell wall skeleton (CWS) from Mycobacterium phlei and Monophosphoryl Lipid A (MPL) from Salmonella minnesota 8595, and prepared as an oil-in-water emulsion with squalene and Tween 80. The final concentrations of CWS and MPL per vaccination were 250 µg and 25 µg, respectively. A dose-escalation, phase I clinical trial was designed for up to twelve patients divided among four cohorts. Cohorts I, II, III and IV were designated to receive a total of 0.1 mg, 0.5 mg, 1.0 mg and 1.5 mg of peptide per vaccination, respectively, with up to three vaccinations separated one month apart.

Isolation and Preparation of Peripheral Blood Mononuclear Cells (PBMC).

PBMC were isolated from 50 ml of heparinized whole blood by Ficoll-Hypaque density gradient centrifugation (Lymphocyte Separation Medium; Organon-Teknika, Durham, N.C.) prior to the first vaccination and four weeks after each vaccination. After isolation at each interval, PBMC were cryopreserved under liquid nitrogen in a sterile cocktail of 90% heat-inactivated, pooled human AB serum (Valley Biomedical, Winchester, Va.) and 10% dimethyl sulfoxide (DMSO) (Sigma Chemical Co., St. Louis, Mo.). Basic cellular immune responses to mitogens and antigens were first determined using freshly-thawed, unfractionated PBMC, derived pre-vaccination and post-third vaccination. For all functional assays and cell culture preparation, PBMC were suspended in a RPMI-1640 based-medium, supplemented with 15 mM HEPES buffer (pH 7.4), 2 mM L-glutamine, 0.1 mM non-essential amino acids, 1 mM sodium pyruvate, 50 µM β-mercaptoethanol, 50 µg/ml gentamicin (all from GIBCO/BRL, Gaithersburg, Md.) and 10% heat-inactivated human AB serum (Valley Biomedical). Cell surface phenotype of resting and activated lymphocyte cultures was analyzed by direct immunofluorescence. Cells were treated with the appropriate primary monoclonal antibody (MAb) conjugated to fluorescein isothiocyanate (FITC) (from Pharmingen, San Diego, Calif. or Becton Dickinson, Mountain View, Calif.), fixed with 1% paraformaldehyde and evaluated by flow cytometry using a FACScan (Becton Dickinson) for the percentage of positive cells and mean fluorescent intensity (MFI).

In Vitro Stimulation (IVS) Cycles for Evaluation of $CD4^+$ T Cell Responses.

IVS cycles were established to: (i) amplify detection of a low proliferative response, (ii) compare "pre-immune" to "post-immune" lymphocytes over a period to time for assessment of potential peptide-specific reactivity, and (iii) derive peptide-specific $CD4^+$ T cell lines in culture for detailed phenotypic and functional characterization. For the first IVS cycle, freshly-thawed PBMC ($5\times10^5$/well), derived pre-vaccination and post-third vaccination, were incubated in parallel cultures in 24-well plates (Costar, Cambridge, Mass.) with irradiated (2,000 rads) autologous PBMC ($3-5\times10^6$/well) as antigen presenting cells (APC) plus the immunizing ras peptide (50 μg/ml) and recombinant human IL-2 (10 U/ml, Cetus, Emeryville, Calif.). After incubation for 7 days, viable cells were recovered and retested for peptide-specific reactivity by proliferation assays (see below) and/or re-cultured by continuous weekly stimulation with peptide and IL-2. For subsequent IVS cycles, recovered lymphocytes were maintained at $2-5\times10^5$/well and APC at $5\times10^6$/well. After the third or fourth IVS cycle, autologous PBMC were replaced with Epstein-Barr Virus (EBV)-transformed autologous B cells as APC (i.e. B-lymphoblastoid cell line (BLCL) at $5\times10^5$/well and irradiated at 20,000 rads). Although IL-2 was maintained at 10 U/ml throughout all IVS cycles, the peptide dose was gradually reduced to 5 μg/ml for propagation of only Ag-specific T cell cultures.

IVS Cycles for Evaluation of $CD8^+$ T Cell Responses from $HLA-A2^+$ Patients.

Freshly-thawed PBMC (from ras patients 32 and 33), derived pre-vaccination and post-third vaccination, were enriched in T lymphocytes by passage over nylon wool columns (Robbins Scientific, Sunnyvale, Calif.) and then depleted of $CD4^+$ T cells by negative selection via panning on anti-CD4 MAb-coated T25 flasks (Applied Immune Sciences, Santa Clara, Calif.). For the first IVS cycle, $CD8^+$ enriched lymphocytes ($5\times10^5$/well) were cultured in 24-well plates with irradiated, autologous PBMC ($5\times10^6$/well) as APC which had been preincubated for 3 hours with the appropriate mutant ras peptide (50 μl/ml) plus human $\beta_2$-microglobulin (10 μg/ml) (Calbiochem, San Diego, Calif.). The mutant ras peptide used here [i.e. ras5-14(Asp12)], however, represented a shorter sequence of the original immunogen, which was shown to bind to HLA-A2 (see bioassay below). IL-2 (10 U/ml) was added 3 days later. After an additional 7 days, viable cells ($2-5\times10^5$/well) were re-cultured by weekly stimulation with APC pre-pulsed with peptide/$\beta_2$-microglobulin, and IL-2 added one day later. After the third or fourth IVS cycle, autologous PBMC were replaced with EBV-transformed, autologous BLCL ($5\times10^5$/well) as APC. The peptide does was gradually reduced to 5 μg/ml for propagation of only Ag-specific CTL cultures. CTL activity was evaluated from cultures 5 to 6 days after Ag restimulation.

Proliferation Response.

Freshly-thawed PBMC ($1.5\times10^5$ cells/well) were incubated in 96-well, flat-bottomed plates (Costar) in the absence and presence of mitogens for up to 3 days and antigens for up to 6 days. The mitogens included Phytohemagglutinin-P (PHA-P) and Pokeweed mitogen (PWM) (both from Sigma), while the antigens included tetanus toxoid (kindly provided by Wyeth Laboratories, Marietta, Pa.) and the indicated ras 13-mer peptides. Furthermore, at the end of an IVS cycle, lymphocytes cultures ($5\times10^4$/well) were examined for peptide-specific proliferation using irradiated APC (i.e. PBMC, $5\times10^5$/well or BLCL, $5\times10^4$/well) incubated with varying concentrations of mutant and control ras peptides for up to 3 or 4 days. In all assays, cultures were pulsed with [$^3$H]-thymidine (1 μCi/well; Amersham, Arlington Heights, Ill.) for the final 18-24 hour of their incubation. Cells were collected with a TOMTEC MACH II 96 harvester (Wallace, Inc., Gaithersburg, Md.) and incorporated radioactivity was measured by liquid scintillation spectroscopy (1205 Betaplate flat bed LS counter; Wallace). MHC class I or II restriction was analyzed in MAb blocking experiments using anti-HLA-A, B, C (clone G46-2.6) or anti-HLA-DR, anti-HLA-DP or anti-HLA-DQ (clones TU36, HI43 or TU169, respectively) (all from Pharmingen). Anti-CD4 (clone OKT4) and anti CD8 (clone OKT8) (both from ATCC) were used in functional assays to confirm the phenotype of the responding T cell subset. Results were expressed as the mean cpm±SEM of triplicate cultures or stimulation index, which was calculated by dividing the cpm of experimental cultures (means counts of triplicate wells) by the cpm of unstimulated control cultures (mean counts of triplicate wells).

HLA-A2 Binding Bioassay.

The 174CEM.T2 cell line ("T2"), (transport deletion mutant) as described in Anderson et al, 1993, *J. Immunol.* 151:3407-3419) was used as a bioassay to measure potential functional binding of exogenously-supplied peptides to human HLA-A2, similarly as described (16) with some modifications. Briefly, T2 cells ($1\times10^6$/treatment) were incubated in a 24-well plate overnight in serum-free IMDM medium in the absence and presence of the different mutant ras peptides (50 μg/ml) plus human $\beta_2$-microglobulin (10 μg/ml for Calbiochem or 3 μg/ml of purified protein from Intergen, Purchase, N.Y.). The $CEA_{571-579}$ peptide was included here as a positive control for binding to HLA-A2(17). After incubation, T2 cells were washed free (of unbound peptide and $\beta_2$-microglobulin) and stained by indirect immunofluorescence for the phenotypic expression and potential upregulation of HLA-A2 using a HLA-A2-specific MAb (One Lambda, Canoga Park, Calif.). Additionally, T2 cells were stained with a pan HLA class I MAb, W6/32 and an isotype-matched ($IgG_{2a}$) MAb, UPC-10 (Cappel, West Chester, Pa.). Data were expressed as the MFI of the gated positive cells.

Cytotoxic Response.

Cytotoxicity was examined by a conventional $^{51}$Cr-release assay, as described (6). Briefly, target cells (i.e. T2, C1R-A2, BLCL, K562) were radiolabeled with 200 μCi of $Na_2[^{51}Cr]0_4$ (Amersham) for 60 minutes at 37° C., followed by thorough washing to remove unincorporated isotope. Effectors and targets ($1\times10^4$/well) were incubated in 96-well, U-bottomed plates (Costar) at various effector target (E/T) ratios in the absence and presence of peptide (+/− monoclonal antibody (MAb) directed against CD4, CD8 or HLA-A2 molecules (clone BB7.2 from ATCC)) for up to 6 hours. After incubation, supernatants were collected using a Supernatant Collection System (Skatron, Sterling, Va.) and radioactivity measured in a γ-counter (Packard Instruments, Downers Grove, Ill.). Cytotoxic activity was defined as percent specific release of $^{51}$Cr and determined by the equation: [(experimental$_{cpm}$−spontaneous$_{cpm}$)/maximum$_{cpm}$−spontaneous$_{cpm}$)]×100.

Results were expressed as the mean±SEM of triplicate cultures. The C1R-A2 line is a BLCL transfected with the HLA-A2 gene (obtained from Dr. P. Creswell, Yale University) (Storkus et al, 1987 *J. Immunol.* 138:1657-1659), and K562 is an erythroleukemia cell line (ATCC, Rockville, Md.) used to measure NK activity.

Immunoassays for Detection of Mutant K-ras Protein in Human Tumor Cell Lines.

Proliferation Response.

Normal and mutant ras proteins were derived from various tumor cell lines (ATCC) which included: Calu-1, a lung carcinoma with a Cys12 mutation; SW480, a colon carcinoma with a Val12 mutation; and HT-29, a colon carcinoma with no known ras codon 12 point mutation (1,18,19). Detergent-lysates were produced aseptically from each cell line by extraction (at $10^7$ cells/ml) in buffer containing: 10 mM Tris-HCl, pH 7.4; 150 mM NaCl; 1 mM EDTA; 1% NP-40; and protease inhibitors (2 μg/ml aprotinin; 0.2 mM PMSF; 0.5 μg/ml leupeptin). After extraction in non-ionic detergent and removal of nuclei and debris, protein concentrations in lysates were determined by the BCA Protein Assay Reagent (Pierce, Rockford, Ill.) and aliquots were stored at −70° C. until analysis. In order to specifically separate and capture ras proteins from these cellular extracts, they were incubated on wells (of 96-well, flat-bottomed plates; Costar) pre-coated with a pan-ras MAb, clone RAS 10 (Oncogene Science, Cambridge, Mass.). Clone RAS 10 previously has been used as a capture MAb in a sandwich ELISA (20). Briefly, plates were coated with RAS 10 (3 μg/ml in 0.05 ml/well or 0.15 μg/well) suspended in 0.1 M carbonate buffer (pH 9.6) overnight at 4° C. Wells were then washed with PBS and blocked with PBS containing 5% BSA for 60 minutes at 37° C. Lysates were added at specific protein concentrations and incubated overnight at 4° C. with additional BSA (0.5%) and extraction buffer to achieve a final volume of 0.1 ml. Control wells received diluent only (i.e. extraction buffer). Plates were washed thoroughly (6 to 8 times) with culture medium in preparation for the proliferation assay.

Flow Cytometry.

Each cell line was examined for the expression of intracellular ras p21 proteins, independent of mutation, by flow cytometry also using the pan-ras MAb, clone RAS 10 (Oncogene Science protocols). Cells were washed to remove serum, fixed with 2% paraformaldehyde for 10 minutes at room temperature (at $10^6$ cells/ml), washed and maintained in PBS buffer containing 10% heat-inactivated goat serum (GIBCO/BRL) plus 0.1% saponin (Calbiochem). Afterwards, cells were treated with the appropriate primary MAb, followed by secondary staining with FITC-conjugated affinity-purified, goat anti-mouse IgG (Southern Biotechnology, Birmingham, Ala.) and analyzed.

TABLE 1 ras p21 Expression in Carcinoma Cell Lines As Measured By Flow Cytometry

| | | Percent Positive Cells (MFI) b | | | |
| --- | --- | --- | --- | --- | --- |
| | | | anti-ras (μg/ml) | | |
| Cell Line a | isotype | anti-class I | 10 | 3 | 1 |
| Calu-1 | 1.0 | 93.4 | 90.6 | 87.8 | 59.8 |
| | | (1617.0) | (331.8) | (224.8) | (176.4) |
| SW480 | 5.3 | 84.2 | 83.4 | 82.8 | 67.0 |
| | | (1184.6) | (630.9) | (386.0) | (273.4) |
| HT29 | 11.6 | 93.5 | 93.1 | 83.4 | 58.6 |
| | | (1313.7) | (422.8) | (303.9) | (232.9) | a See Table 4.
b Each cell line was examined for the expression of intracellular ras p21 protein (independent of mutation) by flow cytometry using the pan-ras MAb, clone RAS 10, at different concentrations. W6/32 was included as a positive control for anti-MHC class I staining, while UPC-10 was included as an isotype-matched (IgG2a) control. Results are expressed as percent positive cells with mean fluorescence intensity (MFI) shown in parentheses.

Enzyme Immunoassay.

Similarly, each cell line was also examined for the expression of intracellular ras p21 proteins, independent of mutation, by an ELISA. As described above, plates were coated with RAS 10 (0.15 μg/well) suspended in 0.1 M carbonate buffer (pH 9.6) overnight at 4° C. At the same time, lysates (300 μg of protein) or diluent control were incubated in separate polypropylene tubes with MAb clone Y13-238 (1 μg/ml) (Oncogene Science), which is reactive with both K-ras and H-ras proteins (21) or an isotype-matched MAb (rat $IgG_{2a}$ anti-mouse B7.1; Pharmingen). The next day, wells were washed with PBS and blocked with PBS containing 5% BSA for 60 minutes at 37° C. The diluent control or lysates, at specified protein concentrations were added and incubated overnight at 4° C. with additional BSA (0.5%) and extraction buffer to achieve a final volume of 0.05 ml. Plates were washed 6 times with PBS containing 0.05% Tween 20 (PBST), and incubated for 60 minutes at room temperature with an affinity-purified, goat anti-rat IgG conjugated to horseradish peroxidase (1:1,000 dilution; Southern Biotechnology). Plates were washed 6 times with PBST and the reactions were visualized following the addition of the chromogen o-phenylenediamine dihydrochloride (Sigma) and hydrogen peroxide and measured at an absorbance of 490 nm using an ELISA microplate autoreader (Bio-Tek Instruments, Winoski, Vt.).

TABLE 2 ras p21 Expression in Carcinoma Cell Lines as Measured by Enzyme Immunoassay

| | | Immunoreactivity ($A_{490}$) b | |
| --- | --- | --- | --- |
| | | anti-ras (μg protein) | |
| Cell Line a | isotype | 75 | 7.5 |
| Calu-1 | 0.299 | 1.496 | 1.288 |
| SW480 | 0.333 | 1.587 | 1.496 |
| HT29 | 0.283 | 1.487 | 0.990 |
| None c | 0.288 | 0.306 | 0.345 | a See Table 4.
b Detergent lysates were isolated from each cell line, and examined for the presence of intracellular ras p21 proteins (independent of mutation) by a sandwich ELISA. To determine anti-ras reactivity, cellular extracts were normalized to the same protein concentrations, as shown. The pan-ras MAb, clone RAS 10 (see Table 2) was used for "capture", while the ras MAb, clone Y13-238, which is reactive with both K-ras and H-ras proteins, was used for "detection". Rat anti-mouse B7.1 was included as an isotype-matched (rat IgG2a) control. Results are reported at $A_{490}$ as the mean of triplicate wells.
c Control wells contained diluent (i.e., extraction buffer) in lieu of lysates.

Example 2

Vaccination of Cancer Patients With Mutant Ras Peptides and Production of Anti-Mutant ras-Specific, MHC Class II-Restricted CD4+ T-Cell Lines A peptide-based, phase I clinical trial was initiated in metastatic carcinoma patients whose tumors harbor point mutations in the ras p21 proto-oncogenes at codon 12. Selected patients were vaccinated with a mutated ras 13-mer peptide spanning positions 5-17, which corresponded to the specific point mutation at codon 12 found in their cancer. After completion of two of the four cohorts (three patients/cohort), two patients demonstrated peptide-specific cellular immune responses resulting from the vaccination.

Patient 43; Mutant ras5-17(Cys12) Peptide

Figure 1B:
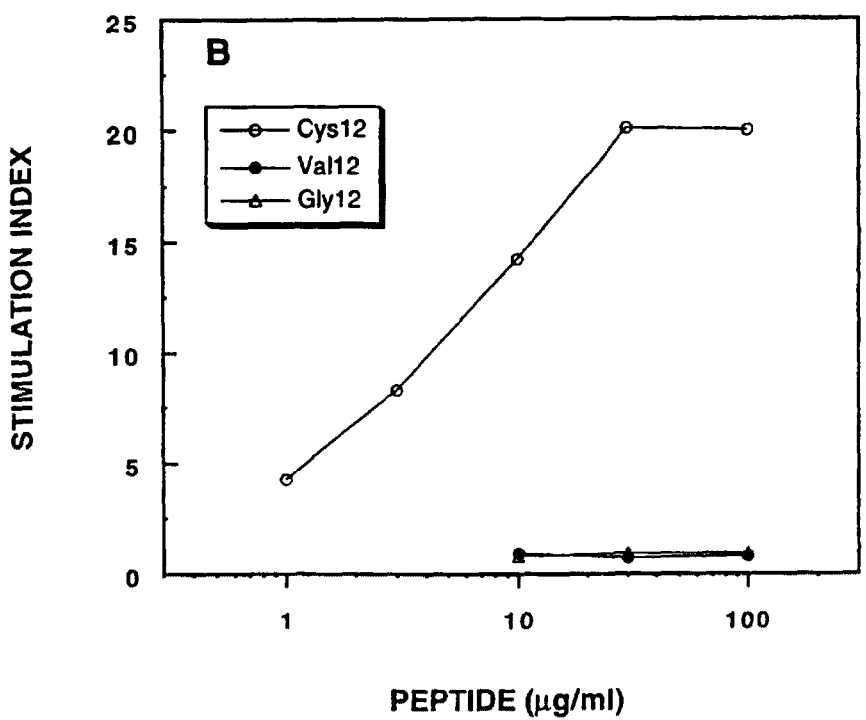

Patient 43 received three complete vaccination cycles of mutant ras5-17(Cys12) peptide, 0.5 mg/vaccination (i.e., cohort II), given in Detox™ adjuvant. Lymphocytes were propagated in vitro by IVS (see Example 1) from post-third vaccinated lymphocytes of RAS patient 43. Antigen-specific, major histocompatibility complex (MHC) class II-restricted CD4+ T-cell lines were established when cultured on the immunizing peptide [i.e., ras5-17(Cys12)] (FIGS. 1A and 1B). Lymphocyte cultures were also derived pre-vaccination from this patient. The lymphocyte cultures were analyzed and compared for peptide-specific cell-mediated immunity (Table 3). Lymphocyte cultures obtained post-vaccination demonstrated a dose-dependent proliferative response following stimulation with the immunizing peptide, as expressed by both cpm and SI values. In contrast, no proliferative response was detectable following incubation with the normal ras5-17(Gly12) peptide, revealing a lack of cross-reactivity with wild-type ras and affirming specificity for recognition of the mutated ras sequence. Moreover, lymphocyte cultures obtained pre-vaccination failed to proliferate in response to stimulation with the mutant ras5-17(Cys12) peptide, even after four IVS cycles on that same peptide (Table 3). While lymphocyte cultures derived post-vaccination continued to proliferate as an Ag-specific cell line in vitro (see FIGS. 1A and 1B, for example), lymphocyte cultures derived pre-vaccination began to show a substantial reduction in their capacity to grow by IVS cycle 5. Thus, these results suggest that the proliferative activity expressed by the post-vaccine lymphocyte culture likely resulted from in vivo priming.

The kinetics for the development of this lymphocyte response was examined and illustrated from IVS cycles 3-7, for example (FIG. 1A). Peptide-specific lymphocyte reactivity increased over time, as measured at two different ras5-17 (Cys12) peptide concentrations. These data demonstrated that the strength of the peptide-induced proliferative signal increased by IVS cycle, with no detectable cross-reactivity induced or observed against the wild-type ras sequence. Also, no detectable proliferation was observed using an irrelevant mutant ras5-17 peptide which contained Val in place of Cys at position 12 (FIG. 1B), further demonstrating lymphocyte-specific recognition of the mutant ras5-17(Cys12) peptide.

Figure 2A:
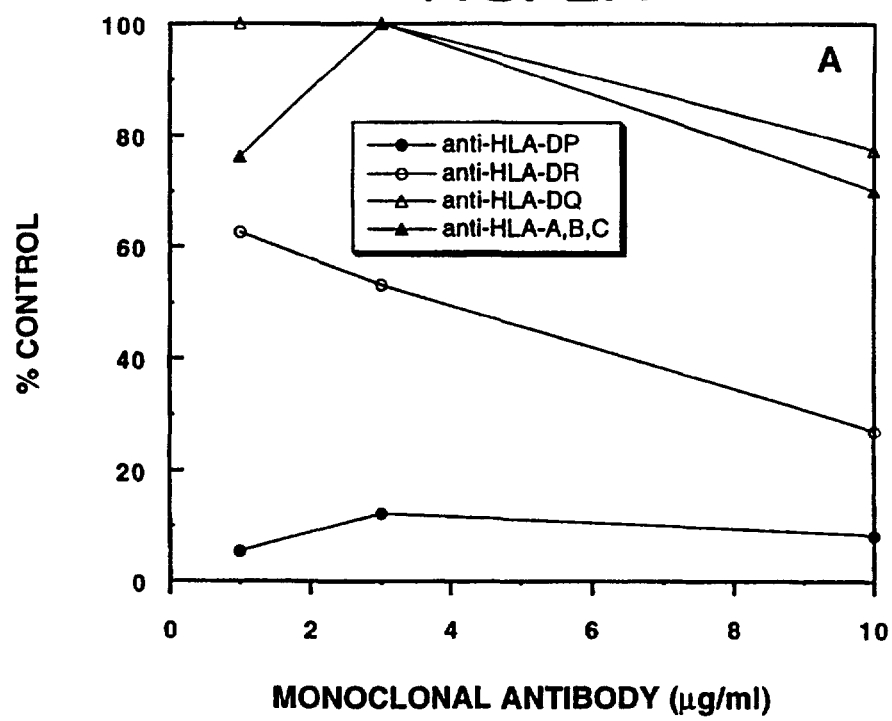
FIGS. 2A and 2B. Proliferation Response by RAS 43 T Cell Line is Mediated by $CD4^+$ Lymphocytes which are MHC class II-Restricted.
Figure 2B:
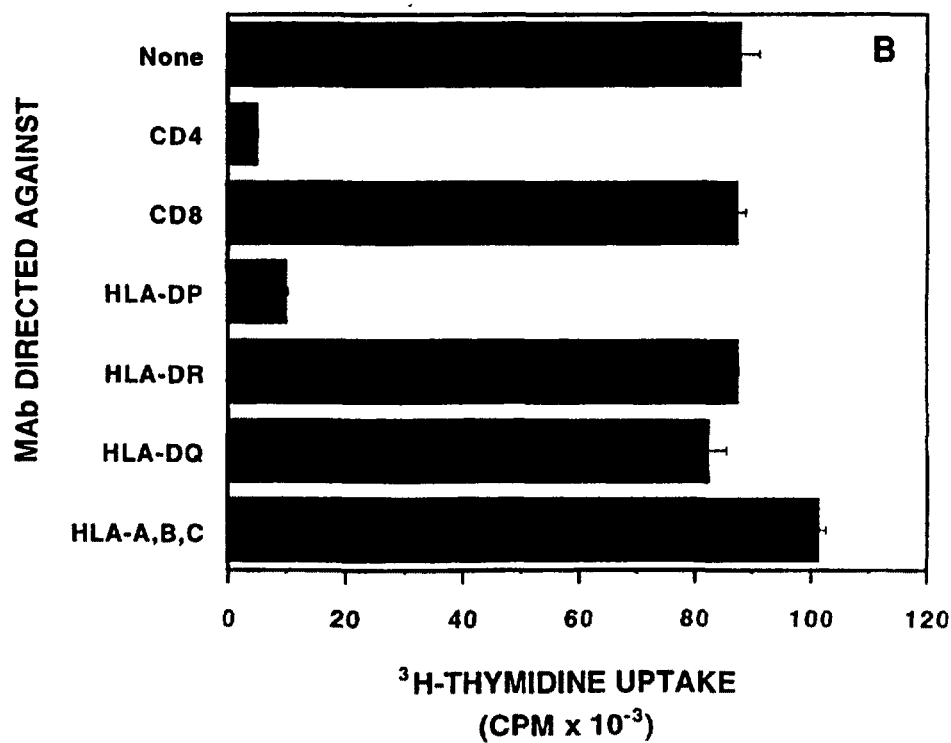
Figure 3:
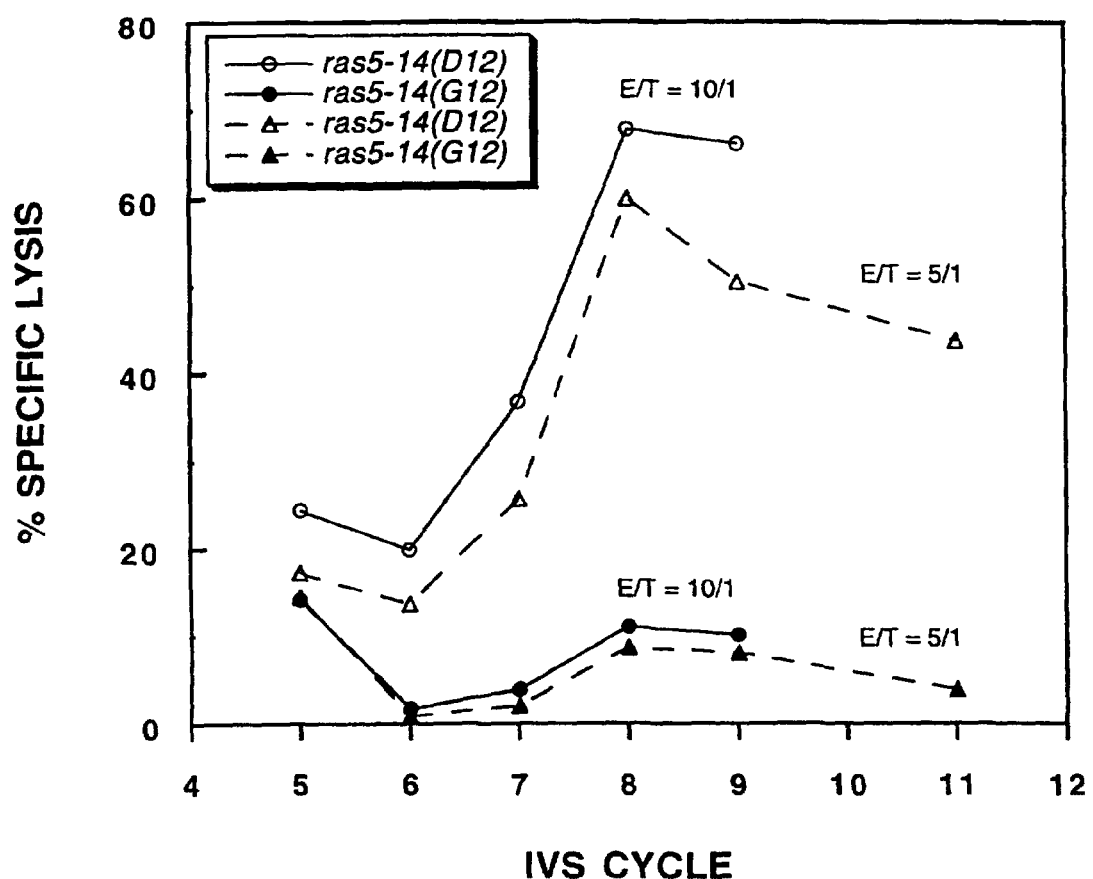
FIG. 3. Generation of a peptide-specific $CD8^+$ T cell line from immune lymphocytes of RAS patient 32. After the third vaccination, PBMC of RAS patient 32 were enriched in $CD8^+$ (46.9%; $CD4^+$, 2.2%) T cells. Cultures were initiated and maintained by continuous weekly IVS cycles using autologous PBMC (up to cycle 3) or BLCL (thereafter) as APC incubated with mutant ras peptide plus $\beta_2$-microglobulin and IL-2. The mutant ras peptide represented a nested HLA-A2 binding, 10-mer sequence [i.e., ras5-14(D12)]. Cytotoxicity was determined weekly by a standard 6 hr $^{51}Cr$-release assay using the T2 cell line as a target, incubated with mutant or normal ras peptide (i.e., 10-mer sequences@ 10 µg/ml), as shown. Results illustrated at E/T ratios of 10/1 and 5/1.

Although flow cytometry revealed the phenotype of this lymphocyte culture to be predominantly CD4+, anti-CD4-MAbs were included in proliferation assays to identify and confirm the functional T cell subset (FIG. 2B). Indeed, anti-CD4 MAb, but not anti-CD8 MAb, inhibited lymphoproliferation, indicating that the peptide-specific proliferative response was mediated by CD4+ T cells. Additionally, MAb directed against nonpolymorphic determinants of HLA class I and II (DP, DR, DQ) molecules were used to define the nature and requirement of MHC restriction for peptide presentation. The proliferation response was determined to be HLA class II-restricted, which mapped to the HLA-DP allele (s), since MAb directed against HLA-DP, but not HLA-DR, HLA-DQ or HLA class I, effectively inhibited peptide-specific stimulation. Thus, vaccination of patient 43 with mutant ras5-17(Cys12) peptide appeared to lead to the in vivo priming of an Ag-specific, HLA-DP-restricted CD4+ T cell response, which was determined in vitro by the production and expansion of the precursor population. Although no specific cytotoxic response was detected against peptide-pulsed autologous EBV-B cells as targets, specific IFN-γ production was detected in response Ag stimulation.

Patient 29; Mutant ras5-17(Val12) Peptide

Patient 29 had a duodenum carcinoma as the primary cancer which harbored a K-ras mutation at codon 12, encoding the substitution of Gly to Val. Patient 29 received three complete vaccination cycles of mutant ras5-17(Val12) peptide, 1 mg/vaccination (i.e., cohort III), given in Detox™ adjuvant. Patient 29 shared an HLA-A2 allele and patient 29's PBMCs were assessed for evidence of both CD4+ and CD8+ T cell responses.

Figure 8A:
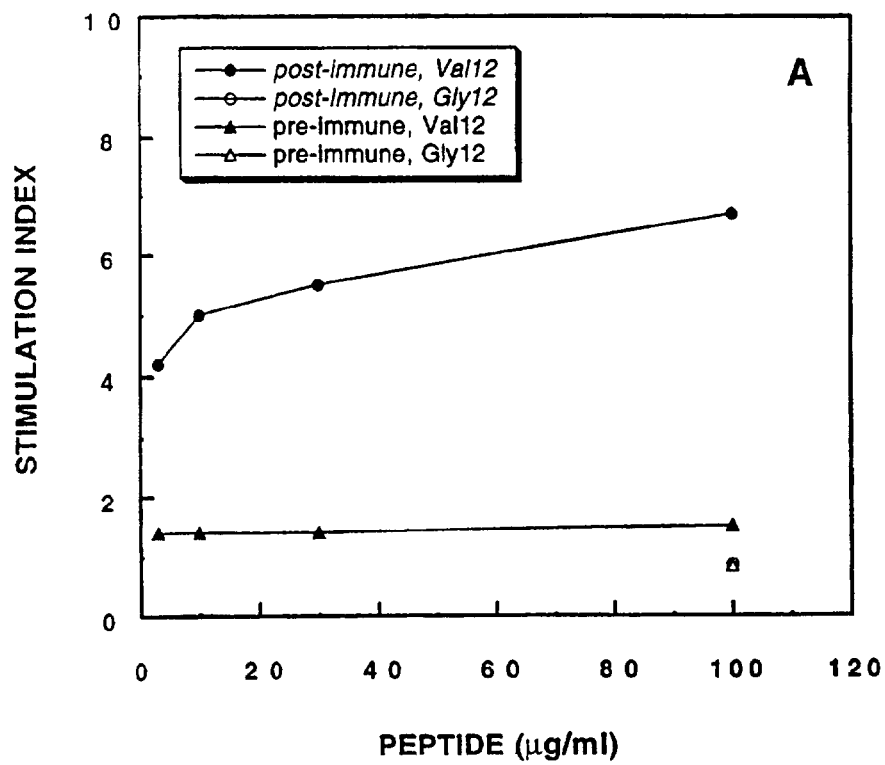
FIGS. 8A and 8B. Production of a peptide-specific CD4+ T cell line from post-vaccinated lymphocytes of patient 29.
Figure 8B:
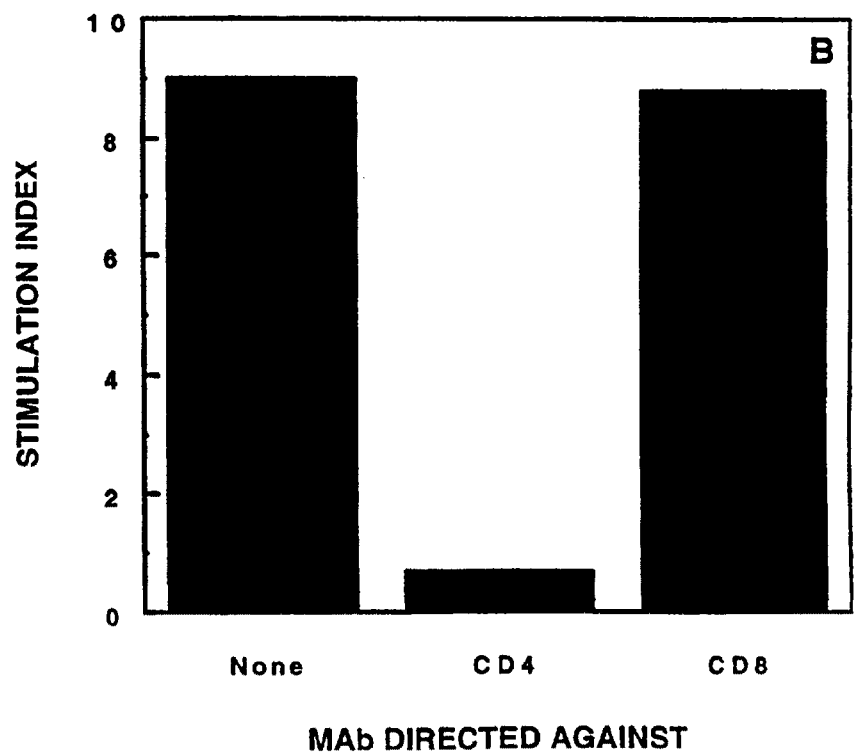

As with patient 43 (Table 3), PBMC from patient 29 obtained post-vaccination and following IVS proliferated in response to stimulation with the immunizing peptide (FIG. 8A). In contrast, no proliferative response was detectable following incubation with the normal ras5-17(Gly12) peptide, thus supporting TCR specificity for recognition of the mutated ras sequence. PBMC cultures obtained pre-vaccination, when assayed in parallel after the same IVS cycle, failed to proliferate in response to stimulation with the mutant ras5-17(Val12) peptide (FIG. 5B). Thus, the proliferative activity expressed by the post-vaccine lymphocyte culture was shown to be likely to result from in vivo sensitization. Also, as with patient 43, an Ag-specific T cell line from postvaccine PBMC of patient 29 was propagated and maintained by IVS with autologous EBV-B cells, antigenic peptide, and IL-2. The peptide-specific proliferative response was demonstrated to be mediated by CD4+ T cells, as anti-CD4 MAb, but not anti-CD8 MAb, inhibited lymphoproliferation (FIG. 8B). Additionally, the proliferative response was shown to be HLA class II-restricted, which mapped predominantly to the HLA-DQ allele, as MAb directed against HLA-DQ, but not HLA-DR, HLA-DP or HLA class L ablated peptide-specific stimulation. Thus, vaccination of patient 29 with mutant ras5-17 (Val12) peptide appeared to result in the in vivo priming of an Ag-specific, HLA-DQ-restricted CD4+ T cell response. As with patient 43, the CD4+ T cell line of patient 29 did not display specific cytotoxicity against peptide-pulsed autologous EBV-B cells as targets, although it did produce IFN-gamma, as well as IL-4, in response to specific Ag stimulation.

Example 3

Ability of the Peptide-Derived CD4+ T-Cell Line of Patient 43 to Recognize the Appropriate Mutant Ras Protein An important immunologic objective was to determine whether the ras peptide-induced T cell lines could also recognize a processed form of the corresponding mutant ras protein, which may be expressed and presented by either the tumor or the APC population. A model system was developed to examine the capacity of the anti-ras5-17(Cys12) peptide-specific CD4+ T cell line of patient 43 to recognize the mutant ras Cys12 protein processed and presented by an autologous APC population (i.e., EBV-B cells) (Table 4). Since a purified or recombinant source of mutant rasCys12 protein was unavailable, the protein was isolated by extraction (with non-ionic detergent) from a human tumor cell, the Calu-1 lung carcinoma, which harbors that particular codon 12 mutation. The HT-29 and SW480 colon carcinoma cell lines, harboring either no known codon 12 mutation or a Val12 mutation, respectively, were used as sources of negative control proteins for monitoring the specificity of the immune reaction. In order to separate and specifically capture total ras proteins from these crude detergent—lysates for biologic presentation by an APC population, they were first incubated on wells (of a 96-well plate) pre-coated with a pan-ras MAb, clone RAS 10, previously characterized as a "capture" MAb in an ELISA format (20). Unbound material was removed from these wells by extensive washing in physiologic buffer and culture medium prior to adding cells.

Using this model system, it was found that the anti-ras-Cys12 peptide-specific CD4+ T cell line, in the presence of EBV-B cells as APC, proliferated in response to the Calu-1 lysate (i.e., "extract") in a dose-dependent fashion (Table 4). The absence of specific CD4+ proliferation using SW480 or HT-29 lysates strengthened the notion for specific TCR recognition of an epitope(s) expressed by the Calu-1-derived ras proteins. Additional control cultures showed productive CD4+ T cell proliferation in the presence of the specific mutant ras5-17 (Cys12) peptide in a dose-dependent fashion and the lack of specific proliferation in the absence of peptide or in the presence of the nonmutated ras peptide sequence (Table 4). The presence of immobilized pan-ras MAb neither stimulated nor inhibited peptide-induced proliferation.

The combination of both EBV-B cells as APC and immobilized pan-ras MAb was found to be essential in this model system for stimulating CD4+ T cell proliferation to the mutant rasCys12 protein (Table 5). In the absence of EBV-B cells, but in the presence of immobilized pan-ras MAb, no proliferation was observed, indicating that an APC population was required for processing/presentation of the mutant ras protein (Table 5). It was likely that Ag processing events were required by the APC population, since pretreatment of EBV-B cells with chloroquine blocked protein—but not peptide induced proliferation. Conversely, in the absence of immobilized pan-ras MAb or in the presence of an isotype-matched MAb, despite the presence of EBV-B cells, no specific proliferation was observed (Table 5), suggesting that the anti-ras MAb was critical for the specific capture of the Calu-1-derived ras proteins. The inability of SW480 and HT-29-derived lysates to stimulate CD4+ proliferation was unlikely due to the absence or weak expression of the RAS 10 MAb-reactive epitope requisite for efficient binding of ras proteins to such substrate (Table 2).

An enzyme immunoassay was developed, which allowed specific detection of ras proteins captured by the pan-ras MAb (clone RAS 10), independent of the ras mutation intrinsic to a tumor cell line. Using this assay format, demonstrable and comparable levels of binding reactivity were found among the three different tumor cell lines (Table 2), indicating that CD4+ proliferation reflected TCR recognition of a mutant ras epitope uniquely expressed by the Calu-1, but not SW480 or HT-29 lysates (Table 4). Comparable intracellular levels of RAS 10 expression were also observed by flow cytometry by analysis of both percent positive cells and MFI of permeabilized, fixed cells.

TABLE 3

Effect of Peptide Vaccination on Proliferative Response of RAS Patient 43

| Culture[a] | Peptide in assay[b] | Conc. (ug/ml) | Proliferation Response[c] cpm (±SEM) | SI |
|---|---|---|---|---|
| Pre-Immune | Cys12 | 100 | 736 ± 320 | 0.8 |
| | | 30 | 1,015 ± 48 | 1.1 |
| | | 10 | 1,076 ± 8 | 1.2 |
| | | 3 | 875 ± 64 | 1.0 |
| | Gly12 | 100 | 790 ± 456 | 0.9 |
| | | 30 | 849 ± 14 | 1.0 |
| | | 10 | 768 ± 257 | 1.1 |
| | | 3 | 824 ± 255 | 0.9 |
| | None (T cell + APC) | — | 888 ± 31 | — |
| Post-Immune | Cys12 | 100 | 14,711 ± 1322 | 22.0 |
| | | 30 | 7,334 ± 294 | 10.9 |
| | | 10 | 5,730 ± 946 | 8.5 |
| | | 3 | 5,935 ± 272 | 8.9 |
| | Gly12 | 100 | 640 ± 23 | 1.0 |
| | | 30 | 819 ± 142 | 1.2 |

TABLE 3-continued

Effect of Peptide Vaccination on Proliferative Response of RAS Patient 43

| Culture[a] | Peptide in assay[b] | Conc. (ug/ml) | Proliferation Response[c] cpm (±SEM) | SI |
|---|---|---|---|---|
| | | 10 | 725 ± 27 | 1.1 |
| | | 3 | 694 ± 19 | 1.0 |
| | None (T cell + APC) | — | 670 ± 6 | — |

[a]Unfractionated PMBC, pre-vaccination and post-third vaccination. Cultures were derived by continuous weekly IVS using autologous PBMC as APC incubated with mutant ras 13-mer peptide and IL-2. PBMC cultures shown were following fourth IVS.
[b]Mutant, ras5-17(Cys12); normal, ras5-17(Gly12).
[c]Proliferation measured by $^3$H-thymidine uptake. Results expressed as cpm (±SEM of triplicate wells) and stimulation index (SI).

Further, the response was antigen specific and MHC class II-restricted (FIGS. 2A and B).

TABLE 4

CD4+ T Cell Line of RAS Patient 43 Proliferates in Response to Mutant K-ras Protein[a]

| Antigen in assay[b] | Conc.[c] | K-ras Mutation[d] | Proliferation Response[e] |
|---|---|---|---|
| Cys12 peptide | 30 | — | 112,354 ± 413 |
| | 10 | — | 109,519 ± 4942 |
| | 3 | — | 116,529 ± 4947 |
| | 1 | — | 48,732 ± 473 |
| Gly12 peptide | 30 | — | 8,130 ± 314 |
| None (T cell + APC) | — | — | 6,836 ± 307 |
| Calu-1 extract | 250 | Cys12 | 64,357 ± 2824 |
| | 75 | | 55,540 ± 1172 |
| | 25 | | 6,884 ± 445 |
| SW480 extract | 250 | Val12 | 6,163 ± 1073 |
| | 75 | | 4,963 ± 1075 |
| | 25 | | 7,682 ± 248 |
| HT-29 extract | 250 | None (Gly12) | 6,955 ± 384 |
| | 75 | | 7,223 ± 179 |
| | 25 | | 6835 ± 119 |

[a]The CD4+ T cell line of RAS patient 43 (see Table 3) now maintained in culture using autologous BLCL as APC.
[b]Assay wells pre-coated with pan-ras MAb clone RAS 10 (0.15 μg/well) before addition of cellular extracts or extraction buffer. Wells then thoroughly washed before addition of APC (i.e., BLCL), T cells ± peptides. Control experiments revealed no effects of the pan-ras MAb on peptide-induced proliferation. Calu-1, lung carcinoma; SW480 and HT-29, colon carcinomas.
[c]Peptide expressed as μg/ml; cellular extract or lysate expressed as μg protein.
[d]Corresponds to K-ras mutation at codon 12 and confirmed by PCR analysis.
[e]Proliferation measured by $^3$H-thymidine uptake and results expressed as cpm ± SEM of triplicate wells (cpm of irradiated BLCL = 4,181 ± 330).

Example 4

Identification of a Nested Peptide Sequence with MHC Class I (HLA-A2) Binding Activity The induction of CD8+ T cell reactivity was examined. Such CD8+ T cell activity could have occurred concomitantly with, or in the absence of, the CD4+ T cell response. In this regard, in vivo priming of the CD8+ T cell response could result from the in vivo processing of the immunogen with the subsequent generation of MHC class I-reactive epitopes. In a murine model, overlapping MHC class II-restricted CD4+ and MHC class I-restricted CD8+ CTL peptide epitopes reflecting the ras Val12 mutation were identified. To this end, the ras5-17 peptide sequences were scanned for putative HLA class I consensus anchor motifs reflecting the HLA-A2 allele, as a working model system. The ras 10-mer sequence 5-14, independent of ras mutation, was identified as a potential candidate for HLA-A2 binding, since it contained the preferred dominant anchors, Leu and Val, at the second (i.e., Leu6) and C-terminus (i.e., Val14) positions of the peptide, respectively (43,44). The ras 9-mer sequence 4-12 appeared to satisfy the motif for binding interactions at positions 1 (i.e., Tyr4) and 9 (i.e., Val12). The N-terminal location of the first dominant anchor, Leu, was found at position 3 (i.e., Leu6).

Accordingly, a panel of ras5-14 peptides were synthesized, containing either the mutated or wild-type residues at position 12. Subsequently, the capacity of these ras peptides to bind to HLA-A2 was analyzed by the T2 bioassay and flow cytometry for specific up-regulation of that class I molecule (Table 7). $CEA_{571-579}$, a 9 amino acid peptide which is a CTL epitope restricted by HLA-A2, was included in these experiments as a positive control. Incubation of T2 cells with mutant ras5-14 peptides having either the Asp12, Cys12 or Val12 substitutions, led to enhanced immunostaining with an anti-HLA-A2-reactive MAb as well as with a "pan" class I MAb (W6/32), compared with the no peptide control, thus suggesting functional binding to the HLA class I A2 allele. Additionally, incubation of T2 cells with the wild-type ras5-14(Gly12) peptide resulted in increased anti-HLA-A2 staining, indicating that neither the absence nor the presence of the mutated residue greatly impacted binding to HLA-A2.

The influence of peptide size and relative location of residues surrounding position 12 on HLA-A2 binding were examined using a spectrum of ras peptides (Table 7). The 13-mer ras5-17(Asp12) peptide, for example, which contained the core residues for binding to HLA-A2, did not appear to bind to T2 cells under these (serum-free) assay conditions, suggesting a critical peptide length and/or required location of MHC anchor residues. Similar results were observed with ras5-17(Val12) and ras5-17(Cys12) peptides. Moreover, the specificity of binding of these ras5-14 peptides to HLA-A2 on T2 cells was further illustrated using a set of mutant rasVal12 peptides that: (i) lacked either one [i.e., ras5-13(Val12)] or both [i.e., ras8-16(Val12)] dominant anchor residues, despite having an appropriate length; and (ii) lacked a desirable length, despite having dominant anchor residues in the second and C-terminus positions [i.e., ras5-12 (Val12)].

Example 5

Production of an Anti-rasAsp12-Specific, MHC Class I-Restricted $CD8^+$ T Cell Line from Patient 32

The above-described mutant ras5-14 peptides were used as in vitro immunogens and tested for their ability generate A2-specific $CD8^+$ CTL lines from HLA-A2+ patients, pre- versus post-vaccination to determine whether the ras5-14 peptide sequences represented HLA-A2-restricted, $CD8^+$ CTL epitopes and whether ras peptide vaccination led to the induction of $CD8^+$ T cell responses.

Patient 32, who expressed an HLA-A2 allele, had colon carcinoma as the primary cancer harboring a K-ras mutation at codon 12, encoding the substitution of Gly to Asp. Patient 32 received three complete vaccination cycles of mutant ras5-17(Asp 12) peptide, 0.1 mg/vaccination (i.e., cohort I), administered in Detox™ adjuvant. No specific $CD4^+$ proliferative response was observed by post-vaccine PBMC against the immunizing 13-mer ras peptide even after multiple IVS cycles; however, this did not preclude in vivo processing of the peptide and generation of HLA class I-reactive epitopes for potential in vivo priming of $CD8^+$ T cells.

$CD8^+$ T lymphocytes, isolated pre-vaccination and post-third vaccination from RAS patient 32, were propagated by IVS (Example 1), and then were analyzed and compared for the development of peptide-specific, cell-mediated cytotoxicity against C1R-A2 targets (Table 6). $CD8^+$ lymphocyte cultures obtained post-vaccination began to express peptide-specific, cell mediated lysis starting at IVS cycle 6, with lytic potency increasing over time. No specific cytotoxic response was detectable in the presence of the normal ras5-17(Gly12) peptide, revealing a lack of cross-reactivity with wild-type ras and affirming specificity for recognition of the mutated ras sequence. In contrast, $CD8^+$ lymphocyte cultures obtained pre-vaccination failed to display specific cytotoxicity. Moreover, while $CD8^+$ lymphocyte cultures derived post-vaccination continued to proliferate efficiently as an Ag-specific cell line in vitro (Table 6), $CD8^+$ lymphocyte cultures derived pre-vaccination lost their capacity to grow beyond IVS cycle 7. Thus, the cytotoxic activity expressed by the post-vaccine lymphocyte culture of patient 32 likely resulted from in vivo priming, and the ras5-14(Asp12) peptide sequence reflected a HLA-A2-restricted $CD8^+$ CTL epitope.

Figure 7:
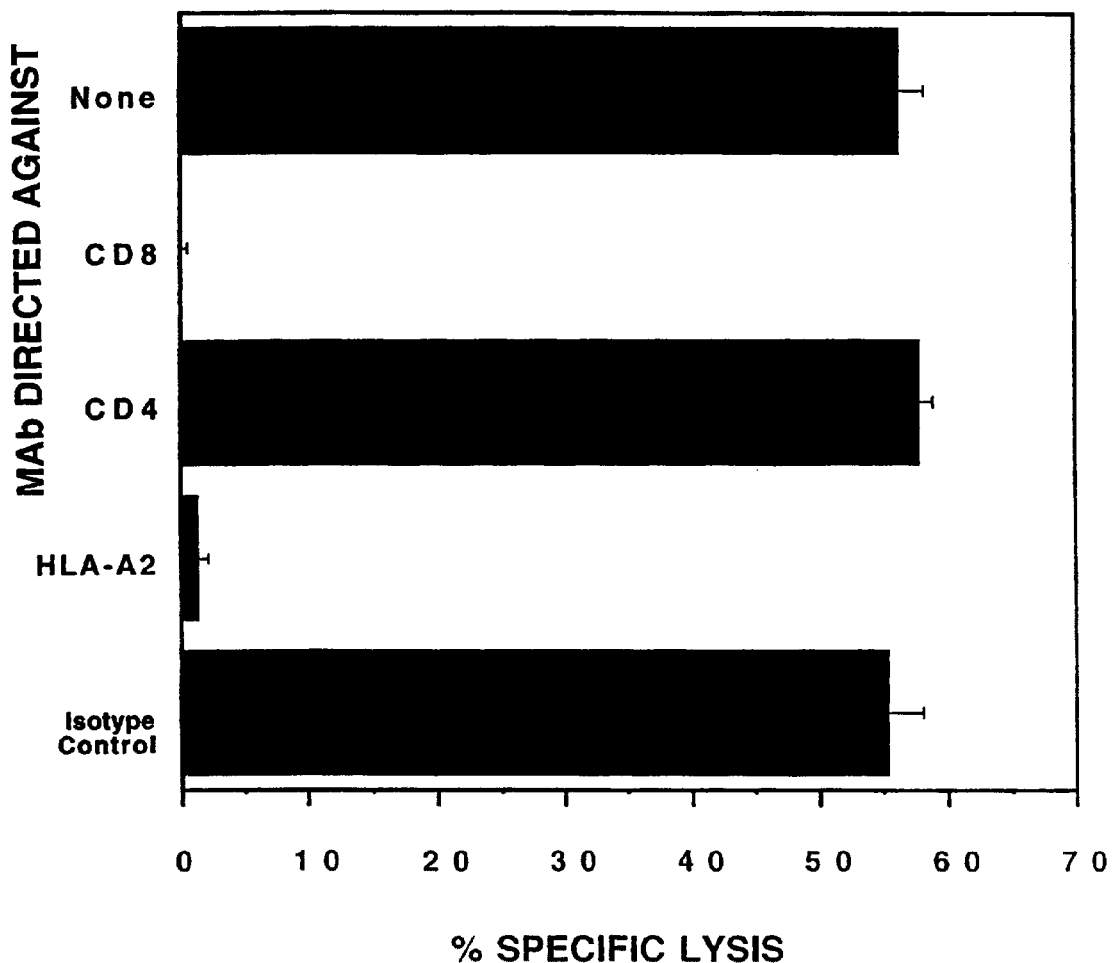
FIG. 7. Cytolytic activity by CD8+ CTL line of patient 32 is HLA-A2-restricted. The requirement for HLA-A2 in peptide presentation (by C1R-A2 targets) was determined in blocking experiments using MAb (clone BB7.2; ascites=1:100 dilution) directed against that molecule (or an isotype-matched MAb). IVS cycle=16; effector/target ratio=10/1; ras5-14(Asp12)peptide=1 µg/ml. MAb directed against the CD4 (clone OKT4; hybridoma supernatant, 20% v/v) or CD8 (clone OKT8; hybridoma supernatant, 20% v/v) molecules were used to identify and confirm the functional T cell subset(s). Control lysis in the absence of peptide or in the presence of ras5-14(Gly12) was <3%.

Peptide-specific, cell-mediated cytotoxicity expressed by the T cell line of patient 32 was confirmed to be mediated by $CD8^+$ T cells, as MAb directed against the CD8, but not the CD4, molecule abolished the lytic response (FIG. 7). Additionally, MAb directed against HLA-A2 (clone BB7.2) on the target cell inhibited cytotoxicity (FIG. 7), thus demonstrating a requirement of HLA-A2 for peptide presentation, which was consistent with the binding characteristics of the peptide (i.e., by the T2 bioassay; Table 7).

Figure 5:
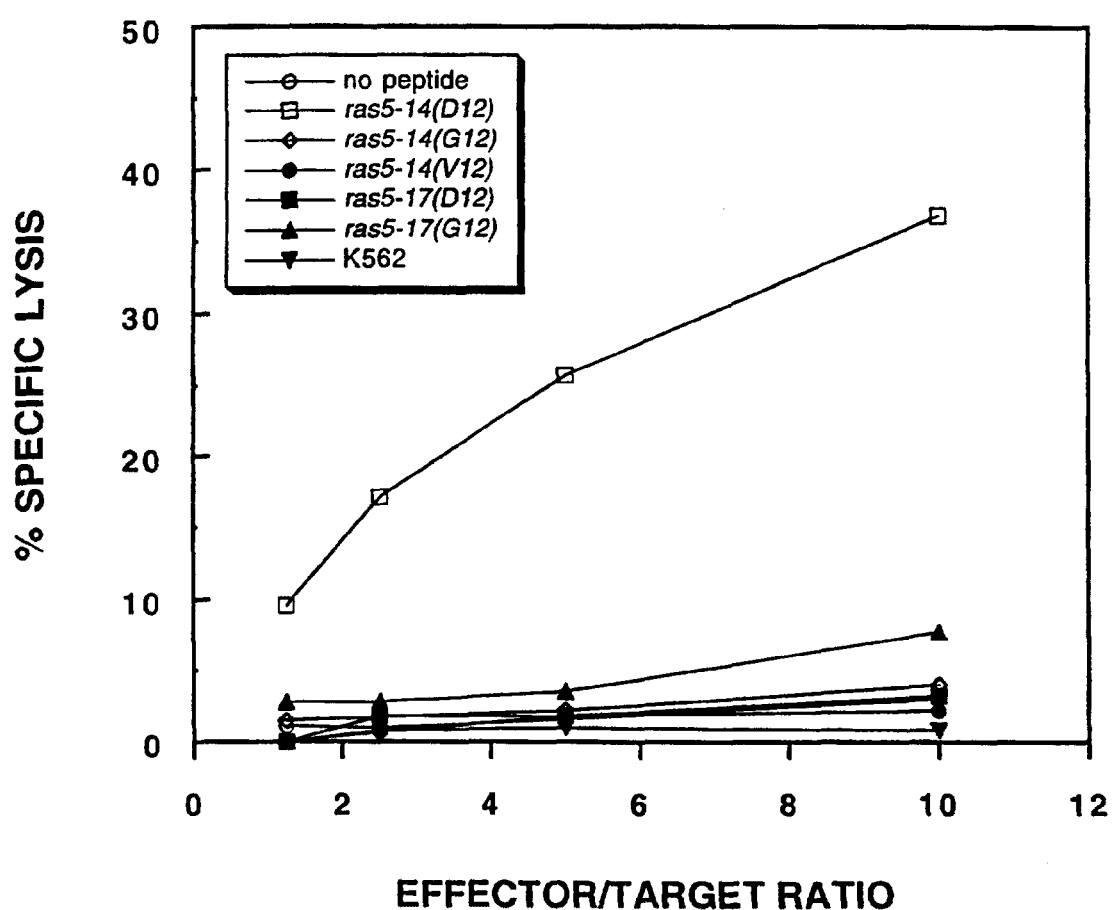
FIG. 5. Cytolytic activity by $CD8^+$ CTL line of RAS patient 32 is peptide-specific. The $CD8^+$ CTL line of RAS patient 32 (see FIG. 3) was assayed against the T2 cell line as a target, incubated with and without different ras peptides (10 µg/ml), as shown. In parallel, the extent of NK activity was evaluated against K562 cells. Cytotoxicity was determined by $^{51}Cr$-release, and the results expressed at different E/T ratios following IVS cycle 7. Similar results were observed using the second, independently-derived $CD8^+$ CTL line as described in Table 6.

The fine specificity for TCR recognition of peptide for lysis was examined using a panel of ras peptides (FIG. 5). Of the ras5-14 peptides tested, only ras5-14(Asp12) sensitized the T2 cell line for lysis. In contrast, ras5-14 peptides, reflecting the wild-type sequence (Gly12) or an irrelevant mutation (Val12), failed to stimulate lysis, despite their ability to bind to HLA-A2 (Table 7). Furthermore, ras5-17(Asp12), which was used as the original immunogen for vaccination, did not appear to induce cytotoxicity under these assay conditions, suggesting a failure to generate the appropriate peptide fragment in vitro and/or to produce a sufficient concentration of the relevant epitope to induce a detectable lytic response. The lack of lysis against K562 cells (FIG. 5) argued against the contribution of NK activity in these cytotoxic reactions. Thus, both amino acid sequence and peptide length were shown to be important for HLA-A2 binding and/or TCR recognition requisite for anti-ras $CD8^+$ CTL-mediated lysis.

Example 6

Production of an anti-rasVal12-Specific, MHC Class I-Restricted $CD8^+$ T Cell Line from Patient 29

The generation of an HLA-A2-restricted $CD8^+$ CTL response was examined in patient 29. As a result of the limited availability of whole blood obtained from this patient (post-third vaccination), a T cell line was generated from unfractionated PBMC without $CD8^+$ T cell enrichment. In addition, because no $CD4^+$ T cell response was observed with pre-vaccine lymphocyte cultures from patient 29 (FIG. 8A), suggesting the unlikelihood for a detectable pre-existing immune response, only post-vaccine lymphocytes were examined for $CD8^+$ T cell reactivity. Also, as described hereinabove, for patients 43 and 32, only the post-vaccine lymphocyte cultures displayed peptide-specific $CD4^+$ or $CD8^+$ T cell activity, respectively. In contrast, under the same culture and assay conditions, no detectable pre-existing peptide-specific immune responses were observed in pre-vaccine lymphocytes of those same patients.

Figure 9A:
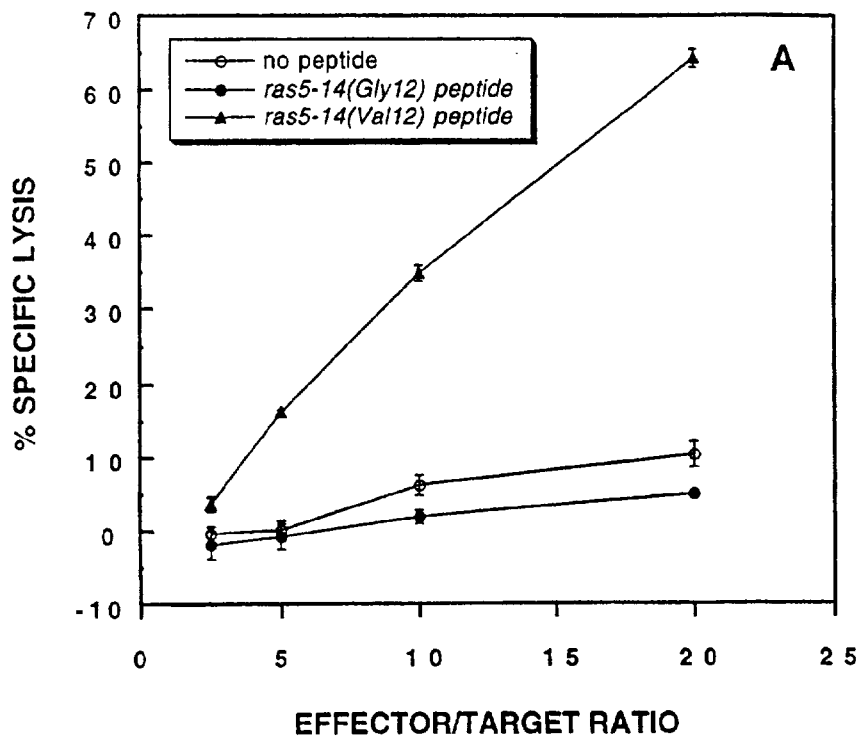
FIGS. 9A and 9B. Production of a peptide-specific CD8+ T cell line from post-vaccinated lymphocytes of patient 29.
Figure 9B:
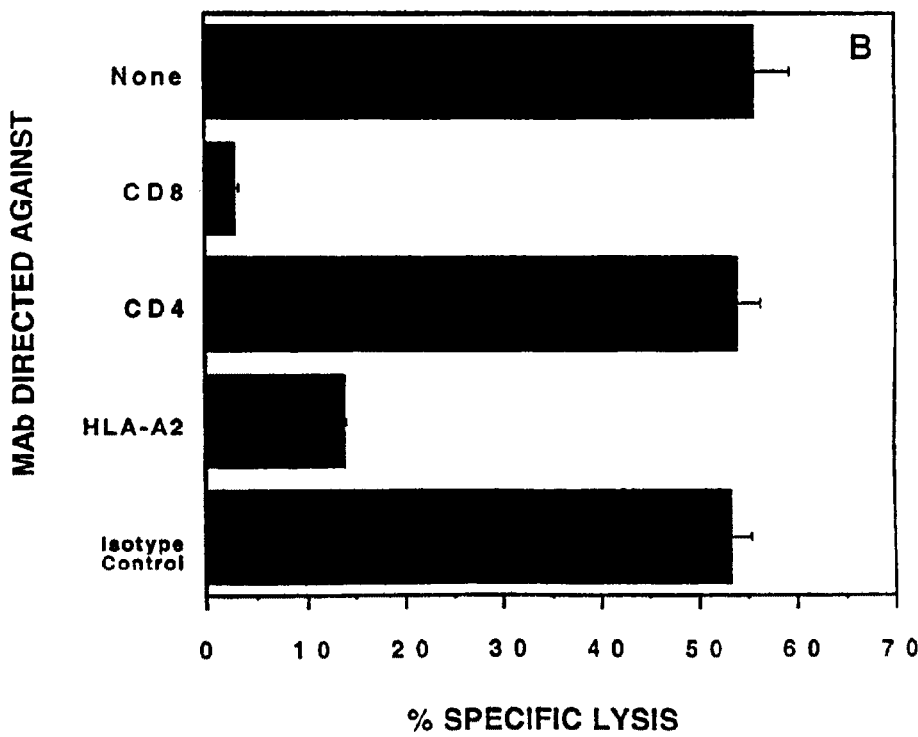

Lymphocytes from patient 29 were propagated in vitro with the homologous mutant ras 10-mer peptide [i.e., ras5-14(Val12) herein] as immunogen, which reflected its ability to bind to HLA-A2 (Table 7). As shown, following IVS cycle 7, such lymphocytes displayed peptide-specific, cell-mediated lysis against C1R-A2 targets incubated in the presence of the ras5-14(Val12) peptide, but not in the presence of the normal ras5-17(Gly12) peptide (FIG. 9A). Peptide-specific, cell-mediated cytotoxicity expressed by the T cell line of patient 29 was shown to be mediated by CD8+ T cells, as MAb directed against the CD8, but not CD4, molecule inhibited the lytic response (FIG. 9B). Phenotypic analysis of this T cell revealed it to be >90% CD8+, as analyzed by IVS cycle 8. In addition, MAb directed against HLA-A2 (clone BB7.2) on the target cell (i.e., autologous EBV-B cells) inhibited cytotoxicity (FIG. 9B), thus demonstrating a requirement for HLA-A2 restriction. In view of the results of this Example and those above, the production of anti-rasVal12-specific CD4+ and CD8+ T cell responses in the same patient was demonstrated (FIGS. 8A, 8B, 9A, 9B).

Studies were also carried out to determine whether such peptide-induced CD8+ CTL could recognize a processed form of the corresponding mutant ras protein. To test this hypothesis, the functional interaction between CD8+ T cells of patient 29 and the SW480 colon carcinoma cell line was examined. SW480 endogenously expressed both the appropriate MHC restriction element (HLA-A2) and the appropriate ras mutation at codon 12 requisite for CTL recognition (18). In contrast to the CD4+ analysis, which measured lymphoproliferation to soluble protein, the CD8+ CTL analysis reflected lytic ability against SW480 cells harboring the naturally-occurring mutation in the absence of exogenously added peptide. Furthermore, SW480 cells were tested untreated or following a short term pretreatment with IFN-gamma, which may be responsible for up-regulating the expression of HLA-A2, as well as other events potentially associated with epitope processing and presentation.

Figure 10A:
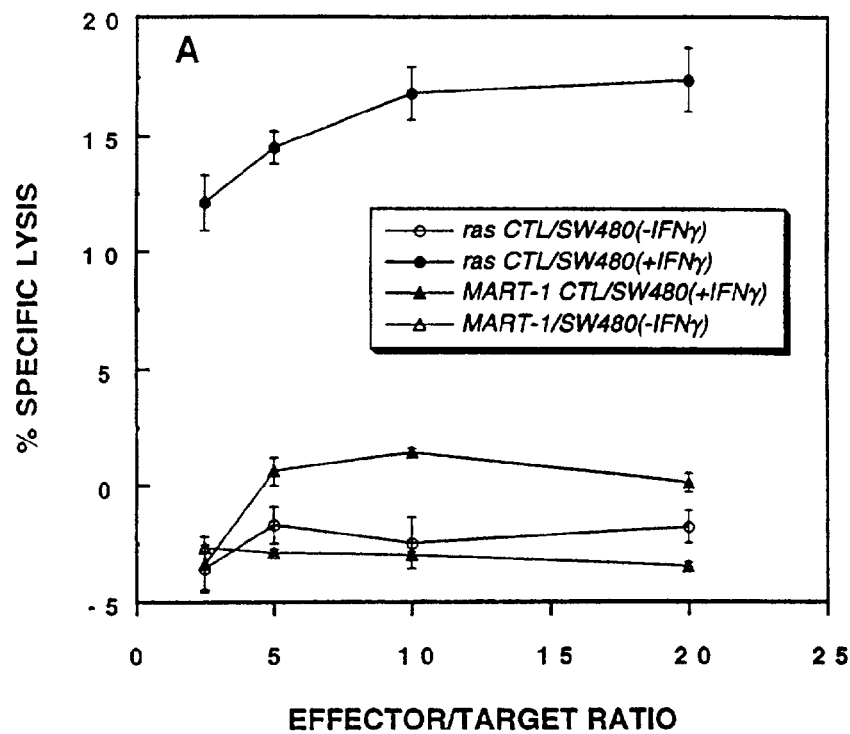
FIGS. 10A and 10B. Anti-ras Val12-specific CTL from patient 29 lyse SW480 tumor targets in the absence of exogenous peptide.
Figure 10B:
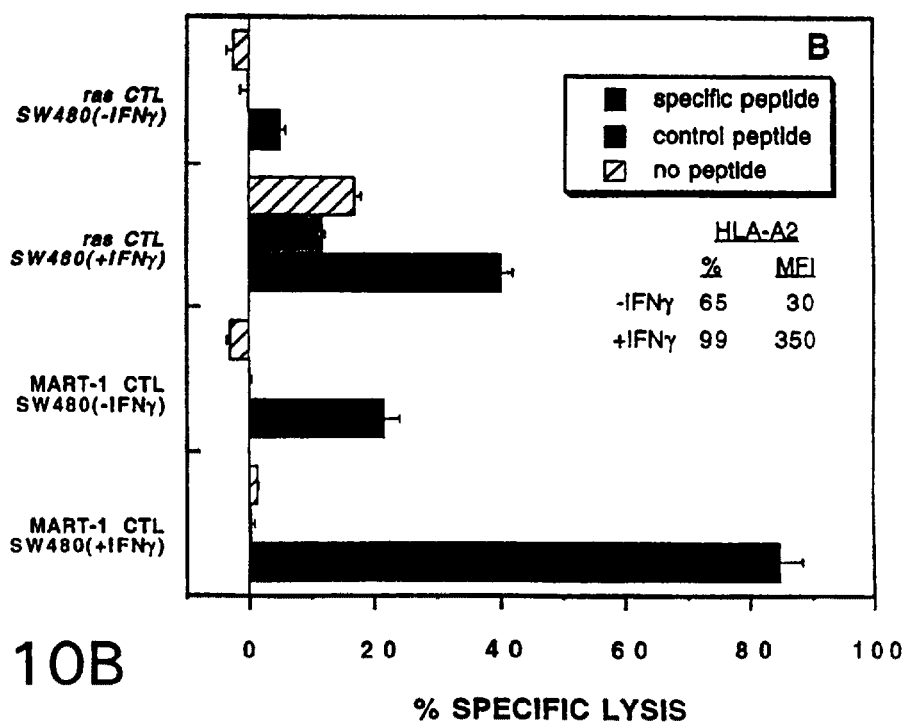

Under these assay conditions, IFN-gamma (IFN-γ) pretreatment enhanced the percentage of SW480 cells positive for HLA-A2 and the density of HLA-A2 molecules per cell based on the MFI without inducing detectable alterations in the expression of the rasVal12 protein as determined by ELISA. In the absence of IFN-γ pretreatment, no CTL lysis was detectable; however, following IFN-γ, pretreatment, demonstrable cytotoxicity was observed at multiple effector/target ratios (FIG. 10A), which correlated with enhanced HLA-A2 and ICAM-1 expression on SW480 cells. Effector cell specificity of lysis was revealed by the inability of an irrelevant HLA-A2-restricted, CD8+ CTL line (i.e., anti-MART-1$_{27-35}$ peptide-specific) to lyse SW480 cells (with or without IFN-γ) (FIG. 10A), unless the appropriate exogenous peptide was added (FIG. 10B). Anti-MART CTL also failed to lyse SW480 target cells (with or without IFN-γ) in the presence of exogenously added ras5-14(Val12) peptide (FIG. 10B), thus demonstrating specificity for recognition of MART-1, but not ras epitopes.

By contrast, anti-rasVal12 CTL-mediated lysis of SW480 cells was enhanced in the presence of exogenously added ras5-14(Val12) peptide, but not wild-type ras peptide, suggesting that the presentation of the endogenously-produced mutant ras epitope(s) was limiting. Target cell specificity for lysis was revealed by the inability of anti-rasVal12 CTL to lyse HLA-A2+ melanoma cells (with or without IFN-γ), which lacked the rasVal12 mutation in the absence of exogenous peptide. The observation that either CTL line lysed IFN-γ-pretreated SW480 cells more efficiently than untreated SW480 cells when incubated in the presence of their respective relevant peptide may have been due, in part, to the increased expression of cell surface HLA-A2 available for peptide loading, thereby, creating more antigenic complexes for CTL recognition.

TABLE 5

Requirements for CD4+ T Cell Response to Mutant K-ras Protein

| Antigen in assay[a] | Conc.[b] | Ab Coating (+/−)[c] | BLCL (+/−)[e] | Proliferation Response[f] |
|---|---|---|---|---|
| Cys12 peptide | 10 | + | + | 87,889 ± 3329 |
| Gly12 peptide | 10 | + | + | 8,844 ± 753 |
| None (T cell + APC) | — | + | + | 8,642 ± 206 |
| Calu-1 extract | 250 | + | + | 80,534 ± 2207 |
| | | − | + | 7,185 ± 93 |
| | | +[d] | + | 7,315 ± 137 |
| | | + | − | 335 ± 42 |

[a/b]See footnotes "b/c" of Table 4.
[c]Assay wells with (+) or without (−) pre-coating of pan-ras MAb clone RAS 10.
[d]Assay wells pre-coated with an isotype-matched MAb (clone UPC-10).
[e]Assay conducted with (+) or without (−) autologous BLCL as APC.
[f]Proliferation measured by $^3$H-thymidine uptake and results expressed as cpm ± SEM of triplicate wells (cpm of irradiated BLCL = 8,520 ± 225; cpm of T cells alone without BLCL = 339 ± 49).

TABLE 6

Comparison of Cytolytic Activity by CD8+ Cultures of RAS Patient 32 Pre-Immunization and Post-Immunization

| | | Recovery[c] | % Specific Lysis[d] | | |
|---|---|---|---|---|---|
| Culture[a] | IVS Cycle[b] | (fold increase) | Mutant | Control | None |
| Pre-Immune | 6 | 2.3 | 14 ± 0 | 10 ± 1 | 13 ± 1 |
| | 7 | 1.3 | 0 | 0 | 0 |
| | 8 | 0.2 | NA[e] | NA | NA |
| Post-Immune | 6 | 6.5 | 24 ± 2 | 8 ± 0 | 13 ± 1 |
| | 7 | 3.5 | 26 ± 2 | 8 ± 1 | 2 ± 0 |
| | 8 | 7.2 | 67 ± 2 | 10 ± 1 | 8 ± 0 |
| | 9 | 2.5 | 68 ± 4 | 21 ± 2 | 22 ± 0 |

[a]In a second independent experiment, CD8+ T cells were isolated from PBMC, pre-vaccination and after the third vaccination.
[b]Cultures were initiated and maintained by continuous weekly IVS using autologous PBMC as APC (up to cycle 3) or BLCL (thereafter) incubated with mutant ras peptide plus $\beta_2$-microglobulin and IL-2. The mutant ras peptide represented a nested HLA-A2 binding, 10-mer sequence [(i.e., ras5-14(D12)].
[c]Cell growth as depicted by the ratio of cells recovered pre and post each IVS cycle.
[d]Cytotoxicity was determined by a standard 6 hr $^{51}$Cr-release assay using the C1R-A2 cell line as a target, incubated with and without ras peptides (i.e., 10-mer sequences @ 10 μg/ml), as shown. Results illustrated at E/T ratio of 20/1.
[e]NA, no cells available for assay due to lack of growth.

TABLE 7

Identification of Mutant ras Peptides that Bind to Human HLA-A2

| | Monoclonal Antibody Directed Against[b] | | |
|---|---|---|---|
| Peptide[a] | HLA-A2 | Pan Class I | Isotype |
| None | 137.9 | 230.4 | 84.0 |
| ras5-17(D12) | 162.8 | 236.0 | 46.5 |
| ras5-14(D12) | 348.3 | 561.7 | 50.8 |
| ras5-14(G12) | 285.2 | 522.8 | 41.3 |
| ras5-14(C12) | 361.4 | 650.9 | 61.4 |
| ras5-14(V12) | 421.6 | 652.2 | 38.1 |
| ras5-13(V12) | 130.6 | 214.8 | 54.1 |

TABLE 7-continued

Identification of Mutant ras Peptides that Bind to
Human HLA-A2

| Peptide[a] | Monoclonal Antibody Directed Against[b] | | |
|---|---|---|---|
| | HLA-A2 | Pan Class I | Isotype |
| ras5-12(V12) | 165.1 | 265.9 | 44.2 |
| ras8-16(V12) | 146.3 | 223.3 | 39.6 |
| CEA$_{571-579}$ | 679.5 | 991.2 | 48.4 |

[a]ras peptides, reflecting the wild-type sequence and three distinct codon 12 mutations; CEA$_{571-579}$, recently reported as a HLA-A2-restricted, CEA-specific CD8$^+$ CTL epitope, and used here as a positive control peptide for MHC class I binding.
[b]The capacity of each peptide to bind to MHC class I (HLA-A2) was determined by a modification in the T2 bioassay. T2 cells were incubated overnight at 37° C. with the appropriate peptide (50 μg/ml) + purified human β$_2$-microglobulin (3 μg/ml) in serum-free medium. After culture, cells were washed, stained with the appropriate MAb, and specific immunoreactivity evaluated by flow cytometry. Results are expressed as MFI.

Figure 4:
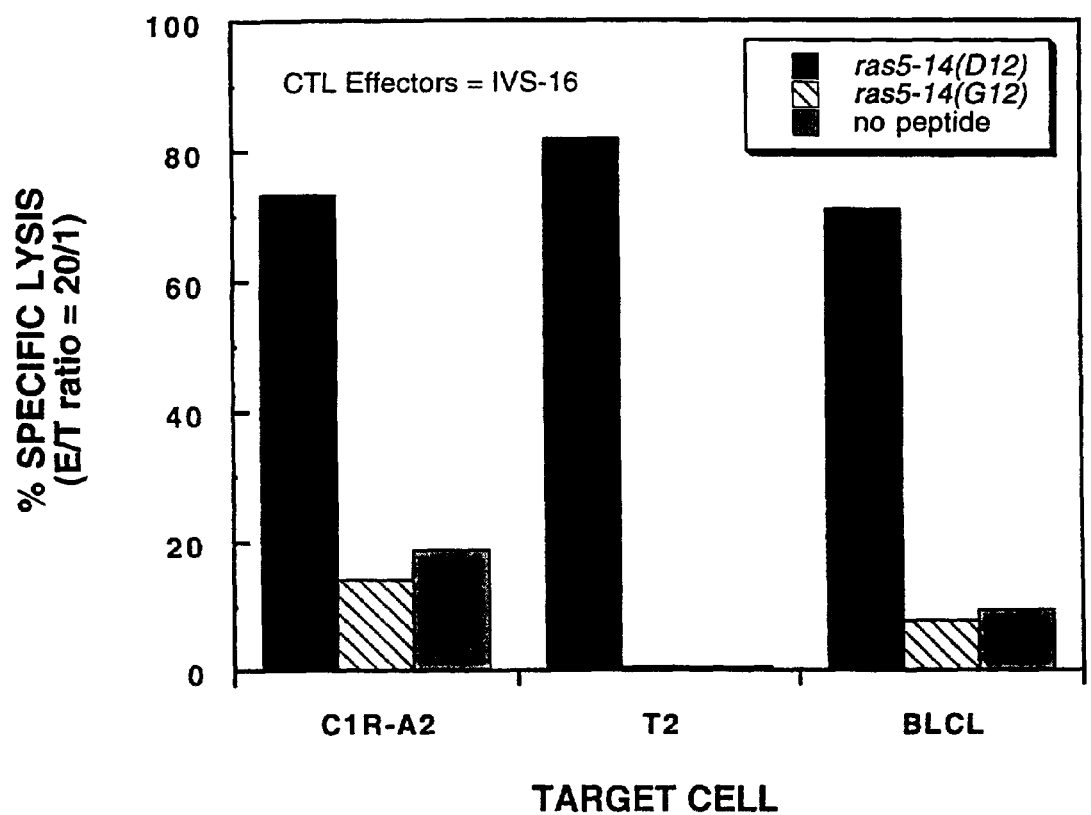
FIG. 4. Cytolytic activity by $CD8^+$ CTL line of RAS patient 32 is HLA-A2-restricted. The $CD8^+$ CTL line of RAS patient 32 (see FIG. 3) was assayed against a panel of HLA-$A2^+$ targets, with and without peptide (10 µg/ml). Cytotoxicity was determined by $^{51}Cr$-release, and the results expressed at E/T ratio of 20/1 following IVS cycle 16. Similar results were observed using a second, independently-derived $CD8^+$ CTL line as described in Table 6. Also, using this second $CD8^+$ CTL line, anti-HLA-A2 MAb (clone BB7.2) inhibited peptide-specific cytotoxicity against C1R-A2 targets (not shown).

In summary, the mutant ras protein surrounding position 12 was examined for potential HLA-A2 peptide binding motifs. An overlapping or "nested" 10-mer peptide was identified [i.e., ras5-14(Asp12)], which was shown to bind to HLA-A2 and display specific functional capacity for expansion of the in vivo-primed CD8$^+$ CTL precursors (FIGS. 4 and 5). Importantly, no specific CTL responses were detectable against the normal proto-ras sequence and no CTL line was produced from pre-immune lymphocytes (Table 6). In contrast to the nested 10-mer peptide, the longer 13-mer peptide used as the immunogen did not show detectable binding to HLA-A2 by bioassay (Table 7) and failed to sensitize targets for lysis in vitro (FIG. 5). Thus, immunization with ras5-17(Asp12) must have been processed in vivo thereby generating the appropriate 10-mer fragment which then led to peptide-specific CD8$^+$ CTL activation. Although initially identified for the Asp12 substitution, ras5-14 peptides reflecting other K-ras mutations at codon 12 were also immunogenic and represent HLA-A2-restricted, mutant ras CD8$^+$ CTL epitopes, as the HLA-A2 peptide binding motif in the ras5-14 sequence remains unaltered.

Example 7

Figure 6:
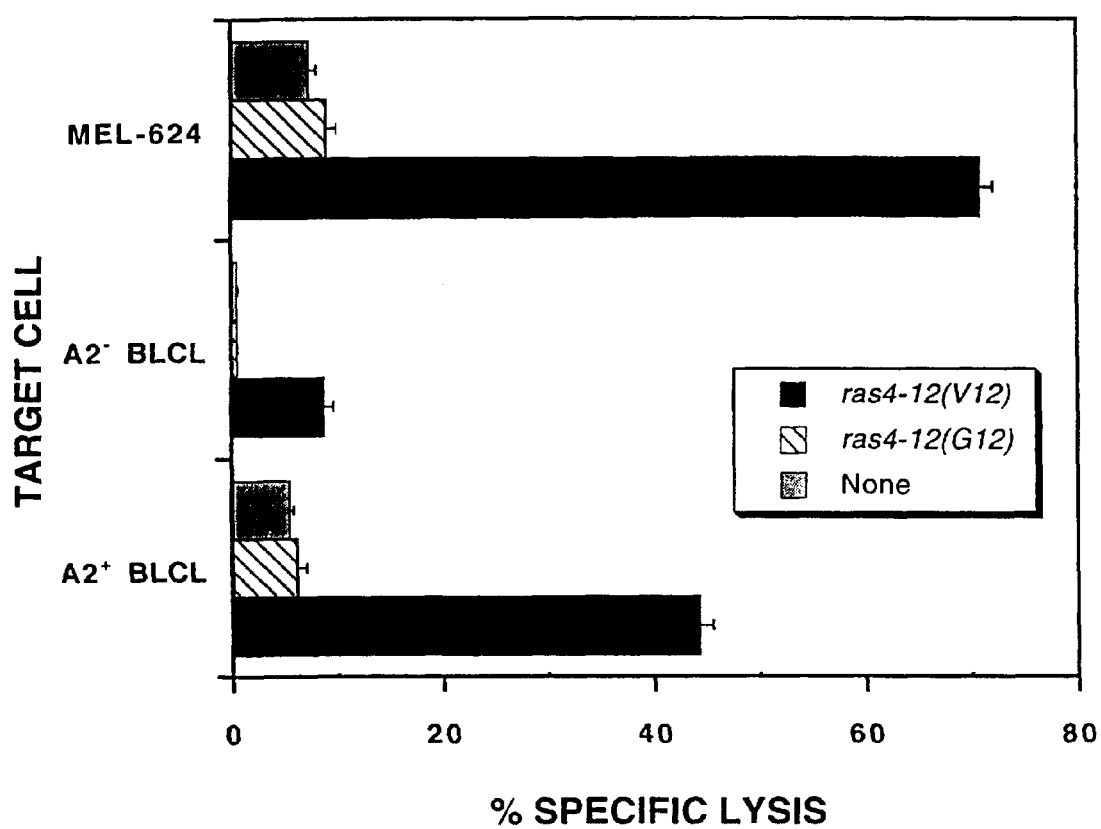
FIG. 6. Generation of a $CD8^+$ T-Cell line specific for the mutant ras4-12(V12) peptide. A $CD8^+$ CTL line specific for ras4-12(V12) was initiated from a normal HLA-$A2^+$ donor using a model antigen presentation system, consisting of the T2 cell line (expressing heightened levels of B7.1), peptide, $\beta_2$-microglobulin and cytokines (IL-2, IL-12). Autologous Epstein Barr Virus-transformed B-cells replaced T2 cells as antigen presenting cells after the second IVS cycle. Here, the importance of both peptide specificity and HLA restriction for cytotoxicity was examined against targets either expressing HLA-A2 (i.e. allogeneic B-cell line matched for HLA-A2 or the melanoma line, MEL-624) or lacking HLA-A2 (i.e. allogeneic B-cell line mismatched for HLA-A2). Cytotoxicity was determined after IVS cycle 6, in the absence or presence of mutant or normal ras peptide (i.e. 9-mer sequences@5 µg/ml) as shown. Results illustrated at effector/target ratio of 20/1 and expressed as mean±SEM of triplicate wells.

Concomitant experiments in the mouse (BALB/c; H-2$^d$) led to the identification of a mutant ras 9-mer peptide reflecting the substitution of Gly12 to Val12 [i.e., ras4-12(V12)], which resulted in the induction of MHC class I-restricted CD8$^+$ CTL responses. The basis of immunogenicity, in part, was attributed to the introduction of the mutated Val12 residue, which created a dominant C-terminus anchor for MHC class I binding. The resulting CD8$^+$ CTL response, thus, likely reflected T cell receptor recognition of a previously unseen peptide/MHC complex. In contrast to the ras5-14 sequence, ras4-12(V12) only partly shared the consensus motif for HLA-A2 binding, as the leucine anchor shifted from position 2 to 3. Importantly, the introduction of the mutated Val12 residue, as in the mouse, now created a dominant C-terminus anchor. Despite the alteration in the preferred location of the putative leucine anchor, the ras4-12(V12) peptide displayed specific, albeit weak, binding to HLA-A2, as detected by bioassay. In contrast, the proto-ras sequence, ras4-12(G12), failed to bind to HLA-A2, demonstrating specificity of binding of the mutant 9-mer sequence. A CD8$^+$ CTL line specific for ras4-12(V12) was then derived from a normal HLA-A2$^+$ individual using a model antigen presentation system, i.e., T2 cells pulsed with exogenous ras4-12 (V12) peptide as APC for the in vitro derivation of antigen-specific CTL. (See FIG. 6).

To further enhance the immunogenic strength of this APC system, additional B7.1 surface expression (for costimulation) was provided on T2 cells by transient infection with a recombinant vaccinia virus (rV-B7.1). In control experiments using an alloreactive system, it was found that under these conditions, B7.1 surface expression on T2 cells increased by 2-3-fold (by MFI), with nominal effect on class I expression, and accelerated the development and/or lytic potency of the resulting allo-HLA-A2-reactive CTL response. This model system was then applied for the generation of a peptide specific CTL response. Indeed, as described herein, a CD8$^+$ CTL line was produced in vitro from a normal HLA-A2+ donor, which displayed peptide specific and HLA-A2-restricted cytotoxicity against peptide-pulsed targets. No lysis was detectable using the wild-type ras peptide to sensitize target cells.

Overall, these findings demonstrate for the first time the definition of mutant K-ras HLA-A2-restricted, CD8$^+$ CTL epitopes at codon 12. Evidence is provided from peripheral blood lymphocytes of both normal individuals and carcinoma patients, which support the hypothesis that vaccination with oncogene-derived peptides induces highly specific and systemic anti-ras cellular immune responses. Moreover, the identification and development of these novel 9-mer or 10-mer mutant ras peptides has important implications for both active (i.e., vaccination) and passive (i.e., ex vivo expansion for cellular adoptive transfer) immunotherapies, which may be used for the induction and propagation of specific CD8$^+$ CTL responses in cancer patients.

Example 8

Identification of Mutant ras CD8$^+$ CTL Peptide Variants

As in the mouse model, potential variants of defined peptide epitopes that may increase i) binding to HLA and ii) the capacity to expand T cell precursors in vitro without altering TCR specificity can be tested in the HLA-A2 system using the mutant ras5-14 peptides reflecting the Asp12 or Val12 substitutions. Although these peptides were identified as HLA-A2-reactive CD8$^+$ CTL epitopes from vaccinated patients, they appeared to exhibit rather weak binding to HLA-A2 (as described above), and required exogenous β$_2$-macroglobulin to further improve MHC/peptide interaction. The identification of peptide variants that strengthen or increase the stability or half-life of the MHC/peptide complex (in vivo and in vitro) may enhance the potency of intrinsically weak immunogenic peptides for the induction and amplification of the relevant T cell response. Since the consensus anchor motif for HLA-A2 is known in the art, putative ras peptide variants will be synthesized reflecting amino acid substitutions at either primary or secondary anchor positions.

Because the ras5-14 sequence already contains the preferred amino acid residues at the dominant anchor positions, 2 (Leu6) and 10 (Val14) of the peptide sequence, they are likely to remain unaltered. Instead, substitutions are introduced at the putative secondary anchor positions, 1 and 3, of the peptide sequence. Candidates include the replacement at position 1 with a Tyr residue or the replacement at position 3 with either a Trp, Leu, Tyr or Phe residue, as well as double substitutions at both positions 1 and 3. Variant peptides reflecting the appropriate ras codon 12 mutation will be synthesized containing these substitutions. In comparative studies with the native peptide sequences, these variants are first examined and screened for their ability to bind to HLA-A2 by the T2 bioassay or a functional competition bioassay which measures inhibition of a control HLA-A2-restricted, Ag-specific CTL response. Variants that display enhanced binding to HLA-A2, are then assessed compared with the native peptide sequences, for their capacity to: (a) sensitize targets for lysis using established anti-ras CTL lines; (b) stimulate proliferation and expansion of established anti-ras CTL lines; and (c) generate anti-ras CTL lines from the original source of immune lymphocytes.

Figure 11:
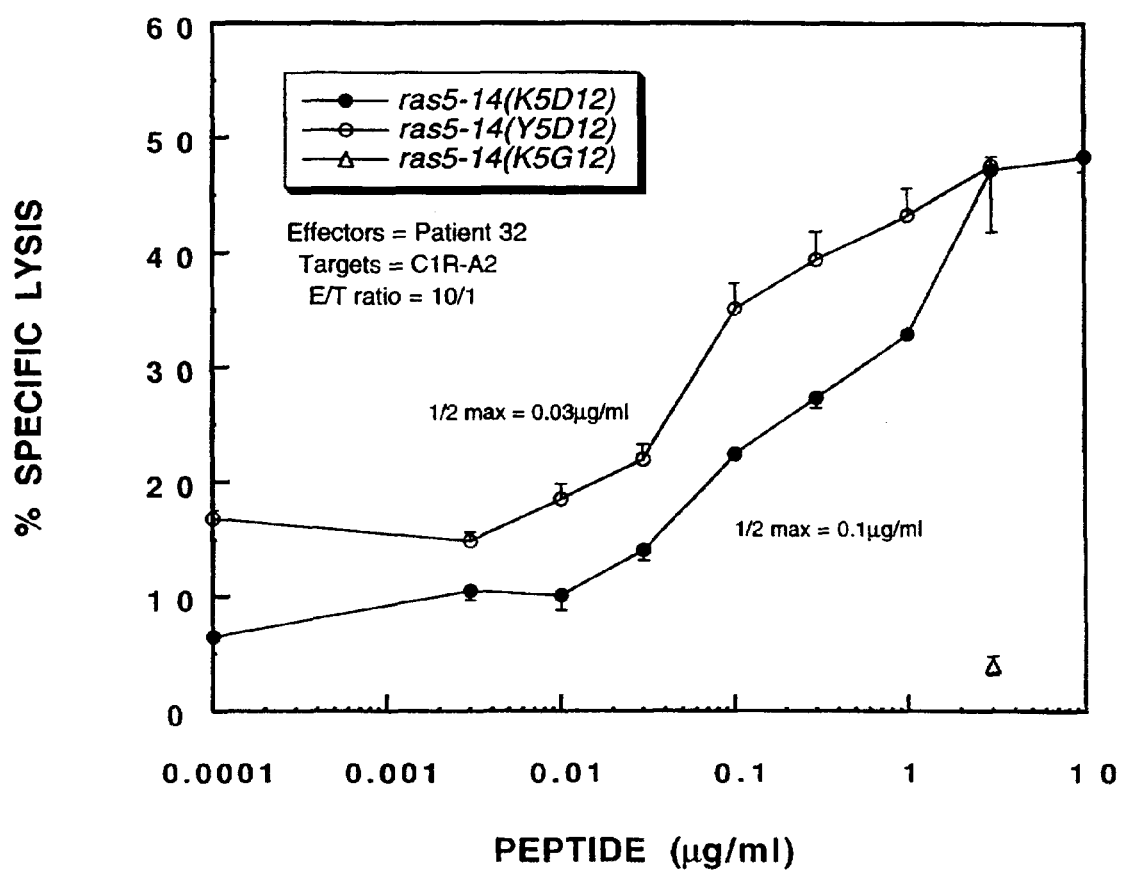
FIG. 11. Identification of a Human Mutant ras CD8+ CTL Peptide Epitope Variant that Enhances Effector Function. The CD8+ CTL line of patient 32 was assayed against the C1R-A2 cell line as a target, incubated with the different ras peptides at several concentrations, as shown. Cytotoxicity was determined by a standard 6 hour $^{51}$Cr-release, and the results expressed at an effector/target ratio of 10/1. Results show that the introduction of a N-terminal Tyr residue (Y5) in mutant ras peptide 5-14(Asp12) enhances CTL activity against peptide-pulsed targets.

Using the anti-ras5-14(Asp12) CTL line in accordance with the present invention, it has been found that single-substituted Tyr and Trp variants displayed higher binding activity than did the native peptide sequence to HLA-A2 on T2 cells, with less dependency for exogenous $\beta_2$-macroglobulin. In addition, the Tyr variant appears to sensitize targets for lysis better than the native peptide sequence, with a shift in the dose-response by three-fold based on half-maximal activity (FIG. 11). The mutant ras peptide 5-14(Asp12), SEQ. ID NO. 3, having an N-terminal Tyr residue (e.g., SEQ. ID NO. 11) enhanced cytotoxic T cell activity against antigen-pulsed target cells.

The identification of such peptide variants, which increase immunogenicity in vitro, promise to be important and effective reagents for subsequent T cell cloning and precursor frequency analysis. Moreover, peptide variants may be used to improve expansion of Ag-specific T cell lines/clones for potential clinical use in adoptive transfer.

Example 9

CD4$^+$ and CD8$^+$ T Cell Subtypes in Cancer

An important aspect of the T cell subset balance is the insight that this balance provides into the immunological basis of disease. Indeed, a host of pathological processes, as determined mainly in model systems of infectious disease, allergy and autoimmunity and, to some extent, cancer have been associated with the balance of the $T_h1/T_h2$ CD4$^+$ subset response and the nature of the resulting cytokine patterns. Little is known regarding the precise roles of Tc1 and Tc2 CD8$^+$ subsets in disease, particularly in neoplasia. Although exceptions to the following patterns may exist, in general, type 1 T cell clones have been shown to principally and selectively secrete IL-2, IFN-$\gamma$ and TNF-$\beta$/lymphotoxin. Type 2 T cell clones have been described to primarily and selectively produce IL-4, IL-5, IL-6, IL-10 and IL-13. Based on the spectrum and functional properties of the different cytokine patterns, type 1 T cells have been implicated in cell-mediated immunity, while type 2 T cells have been proposed to participate in humoral immunity. Accordingly, based on their involvement in cell-mediated immunity, the induction and expression the type 1 T cell response has been proposed as the more relevant and desirable pathway for antitumor reactivity.

Similar to the murine system, in human cancer, potential changes in the development and balance of the "$T_h1/T_h2$" and "Tc1/Tc2" phenotypes can be correlated. To that end, CD4$^+$ and CD8$^+$ T cells are purified from patient peripheral blood lymphocytes obtained pre and post-each vaccination cycle, and stimulated in vitro under maximal conditions with anti-TCR MAb. Thereafter, cytokine levels, e.g., IFN-$\gamma$ and IL4, IL-5 or IL-10, are determined by ELISA or Elispots assays, as prototype cytokines for type 1 and type 2 responses, respectively. Furthermore, cytokine profiles of CD4$^+$ and CD8$^+$ T cell lines produced from immunized patients in response to activation with anti-TCR MAb versus antigenic peptide can be evaluated as a more physiological stimulus. The results from these studies may serve as surrogate endpoints in anti-cancer vaccine clinical trials, and also shed light on potential mechanisms of immune suppression during cancer progression (i.e., bias toward type 2 patterns) and immune enhancement associated with objective tumor responses (i.e., bias toward type 1 patterns). Such correlations may also help in the design of appropriate adoptive transfer culture strategies, such as those described in murine studies, that exploit the identification, selection and amplification of the most relevant T cell subsets.

Example 10 ras Oncogene-Specific T Cells

Isolation and Analysis of Effector Mechanisms

The ability of epitope-specific T cell populations to recognize processed forms of the endogenously-produced oncoproteins expressed by tumor cells is absolutely crucial to the success of techniques such ASI or cellular adoptive immunotherapy. In both normal donors and cancer patients, the present invention relates to the hypothesis of processing and presentation of the corresponding peptides (or closely related sequences) as multiple (sub)dominant epitopes with productive TCR recognition of the antigenic complexes. However, in order to elicit a measurable anti-rasVal 12 CTL response in the absence of exogenous peptide, for example, the SW480 tumor targets, the cells required a short term prior exposure to IFN-$\gamma$. Although the exact mechanisms by which IFN-$\gamma$ acted in this model remain to be fully elucidated, cytotoxicity did correlate, at least in part, with increased expression of HLA-A2, ICAM-1 and Fas (CD95) molecules, suggesting the following nonlimiting and nonbinding theoretical possibilities: (a) the endogenously-produced mutant ras epitopes were limiting, but could be enhanced by increasing the density of class I/peptide complexes available for TCR recognition; (b) the avidity of the CTL/target interaction was weak, but could be enhanced by increasing the density of accessory molecules important for Ag-independent interactions; or (c) tumor cell sensitivity to CTL-mediated lysis via a FasL/Fas-dependent apoptotic pathway was originally defective or weak, but could be restored or enhanced by increasing the density of cell surface Fas. These possibilities, as well as others, may provide explanations by which tumor cells escape immune recognition and attack, which may occur at the level of TCR-MHC/peptide, cell-cell adhesion or the cytotoxic mechanism. Conversely, the observation that cytotoxicity could be enhanced by IFN-$\gamma$ introduces the possibility for the application of IFN-$\gamma$ or IFN-$\gamma$-inducing cytokines, such IL-12, in ASI.

The role of a Fas-dependent pathway in anti-rasVal12 CTL-mediated lysis of IFN-$\gamma$-pretreated SW480 tumor cells can be explored in blocking experiments using commercially-available anti-CD95 MAb (clone ZB4), anti-CD9SL MAb (clones 4H9 or 4A5) or the combination of both for maximum neutralization. Isotype-matched Ab and Fas-sensitive, autologous peptide-pulsed EBV-B cells will be used as appropriate controls. Additional control experiments include a comparison of untreated to cytokine-pretreated SW480 tumor cells for sensitivity to Fas Ab-induced apoptosis/cell death (using commercially-available clones DX2 or CH-11), as determined by isotope release or TUNEL assays. Jurkat or EBV-B cell lines are used as positive controls. Additional support for the role of Fas in the lytic mechanism involves the use of membrane-permeable peptide-based inhibitors, which have been shown to block apoptotic death in Fas-sensitive cell types, such as Jurkat tumor cells. These inhibitors, when preloaded into susceptible cells, specifically block the functional activity of certain endogenous intracellular cysteine proteases (e.g., caspases, most notably ICE-like and CPP-32-like subfamilies) involved in the biochemical pathway of apoptosis. Taken collectively, these experiments can provide insights into the role of Fas and apoptotic pathways in tumor cell susceptibility to CTL-mediated lysis and modulation of their lytic phenotype by cytokine interactions.

Because tumor cell expression of endogenously-derived mutant ras epitopes may be a limiting event affecting CTL lytic efficiency, the isolation of CD8+ T cells within the bulk population is performed. Such T cells may display a higher affinity for recognition of antigens that are present at extremely low-antigen densities. Furthermore, the interaction between higher affinity TCR with MHC/peptide may be of sufficient strength to obviate the need for Ag-independent interactions. As in the murine system, one approach will be based on conventional T cell cloning at limiting dilution and subsequent examination of lytic efficiency against target cells pulsed with titrating amounts of relevant peptide or tumor cells (±IFN-γ pretreatment) harboring the ras oncogene. Clones are expanded on the appropriate mutant ras peptide (or defined peptide variant), with peptide dose gradually reduced over time during culture in an effort to derive and maintain the most Ag-sensitive clones. Similar studies can be conducted for the isolation of peptide-specific CD4+ T cell clones, as determined by their proliferative capacity or cytokine secretion (e.g., IFN-γ) in response to titrating amounts of relevant peptide or exogenous sources of tumor-derived protein. The production and propagation of such oncogene-specific CD4+ and/or CD8+ T cell clones has direct implications for adoptive immunotherapy.

In addition, TCR-αβ-chain usage of ras oncogene-specific T cell clones can be used to evaluate and correlate TCR phenotype (repertoire) with functional response. If predominant or restricted Vα or Vβ patterns are delineated, anti-TCR-specific MAb can be employed for more rapid cell isolation from original bulk or polyclonal populations of immune lymphocytes. The identification of such TCR-αβ patterns may also lead to the development of molecular-based protocols for: (a) tracking the development of the T cell response following each vaccination cycle, as a quantitative measurement for monitoring Ag-specific immune status; and (b) the isolation and cloning of high affinity TCR as an experimental model to explore the capacity to transduce and functionally convert autologous naive lymphocytes into Ag-specific effector cells. The molecular technology for the high efficiency transduction of naive T cell populations with viral expression vectors encoding novel receptor molecules is known to those having skill in the art. The overall objectives of these studies enable the development and exploration of experimental cancer immunotherapy models that combine principles of both gene therapy and immunotherapy, which result in the generation of effector populations for adoptive transfer with modified and enhanced tumor-specific Ag recognition and targeting capabilities.

REFERENCES

1. Bos, J. L. The ras gene family and human carcinogenesis. *Mut. Res.* 195, 255-271 (1988).
2. Bos, J. L. Ras oncogenes in human cancer: a review. *Cancer Res* 49, 4682-4689 (1989).
3. Kiaris, H. and Spandidos, D. A. Mutations of ras genes in human tumors (review). *Int. J. Oncol.* 7, 413-421 (1995).
4. Abrams, S. I., Hand, P. H. Tsang, K. Y. and Schlom, J. Mutant ras epitopes as targets for cancer vaccines. *Sem. Oncol.* 23, 118-134 (1996).
5. Greenberg, P. D. Adoptive T cell therapy of tumors: mechanisms operative in the recognition and elimination of tumor cells. *Adv. Immunol.* 49, 281-355 (1991).
6. Abrams, S. I., Dobrzanski, M. J., Wells, D. T., Stanziale, S. F., Zaremba, S., Masuella, L., Kantor, J. A., and Schlom, J. Peptide-specific activation of cytolytic CD4+ T lymphocytes against tumor cells bearing mutated epitopes of K-ras p21. *Eur. J. Immunol.* 25, 2588-2597 (1995).
7. Tsang, K. Y., Nieroda, C. A., DeFilippi, R., Chung, Y. K., Yamaue, H., Greiner, J W., and Schlom, J. Induction of human cytotoxic T cell lines directed against point-mutated p21 ras-derived synthetic peptides. *Vaccine Res.* 3, 183-193 (1994).
8. Peace, D. J., Chen, W., Nelson, H., and Cheever, M. A. T cell recognition of transforming proteins encoded by mutated ras proto-oncogenes. *J. Immunol* 146, 2059-2065 (1991).
9. Jung, S. and Schluesener, H. J. Human T lymphocytes recognize a peptide of single point-mutated, oncogenic ras proteins. *J. Exp. Med.* 173, 273-276 (1991).
10. Geddle-Dahl III, T. Eriksen, J. A., Thorsby, E. and Gaudernak, G. T-cell responses against products of oncogenes: generation and characterization of human T-cell clones specific for p21 Ras-derived synthetic peptides. *Human Immunol.* 33, 266-274 (1992).
11. Fossum, B., Gedde-Dahl III, T., Hansen, T., Eriksen, J. A, Thorsby, E., and Gaudernack, G. Overlapping epitopes encompassing a point mutation (12 Gly>Arg) in p21 ras can be recognized by HLA-DR, -DP and -DQ restricted T cells. *Eur. J. Immunol.* 23, 2687-2691 (1993).
12. Qin, H., Chen, W., Takahashi, M., Disis, M. L., Byrd, D. R., McCahill, L., Bertram, K. A., Fenton, R. G., Peace D. J., Cheever, M. A. CD4+ T-cell immunity to mutated ras protein in pancreatic and colon cancer patients. *Cancer Res.* 55, 2984-2987 (1995).
13. Fossum, B., Olsen, A. C., Thorsby, E., and Gaudernack, G. CD8+ T cells from a patient with colon carcinoma, specific for a mutant p21-Ras-derived peptide (GLY$^{13}$>ASP), ar cytotoxic towards a carcinoma-cell line harbouring the same mutation. *Cancer Immunol. Immunother.* 40, 165-172 (1995).
14. Van Elsas, A., Nijman, H. W., Van der Minne, C. E., Mourer, J. S., Dast, W. M., Melief, C. J. M. and Schrier, P. I. Induction and characterization of cytotoxic T-lymphocytes recognizing a mutated p21 Ras peptide presented by HLA-A*0201. *Int. J, Cancer* 61, 389-396 (1995).
15. Gjertsen, M. K., Bakka, A., Breivik, J., Saeterdal, I., Gedde-Dahl III, T., Stokke, K. T., Solheim, B. G., Egge, T. S., Soreide, O., Thorsby, E., and Gaudernack. Ex vivo ras peptide vaccination in patients with advanced pancreatic cancer: results of a phase I/II study. *Int. J. Cancer* 65, 450-453 (1996).
16. Salter, R. D. and Cressell, P. Impaired assembly and transport of HLA-A and B antigens in a mutant T×B hybrid. *EMBO J.* 5, 943-949 (1986).
17. Tsang, K. Y., Zaremba, S., Nieroda, C. A., Zhu, M. Z., Hamilton, J. M. and Schlom, J. Generation of human cytotoxic T cells specific for human carcinoembryonic antigen epitopes from patients immunized with recombinant vaccinia-CEA vaccine. *J. Natl. Cancer Inst.* 87, 982-990 (1995).
18. Capon, D. J., Seeburg, P. H., McGrath, J. P. Hayflick, J. S., Edman, U., Levinson, A. D. and Goeddel, D. V. Activation of Ki-ras2 gene in human colon and lung carcinomas by two different point mutations. *Nature* 304, 507-513 (1983).
19. Kahn, S. M., Jiang, W., Culbertson, T. A., Weinstein, I. B., Williams, G. M., Tomita, N. and Ronai, Z. Rapid and sensitive nonradioactive detection of mutant K-ras genes via enriched PCR amplification. *Oncogene* 6, 1079-1083 (1991).
20. Hamer, P. J., La Vecchio, J., Ng. S. DeLellis, R., Wolfe, H. and Carney, W. P. Activated Val-12 ras p21 in cell culture fluids and mouse plasma. *Oncogene* 6, 1609-1615 (1991).
21. Furth, M. E., Davis, L. J. Fleurdelys, B., and Scolnick, E. M. Monoclonal antibodies to the p21 products of the transforming gene of Harvey murine sarcoma virus and of the cellular ras family. *J. Virol.* 43, 294-304 (1982).
22. Takahashi T., Nau, M M, Chiba, I. et al, :P53: a frequent target for genetic abnormalities in lung cancer. *Science* 1998, 246:291-294.
23. Chiba, I., Takahashi, T., Nau M M, et al. Mutation in the p53 gene are frequent in primary resected non small lung cancer. *Oncogene* 1990, %:1603-1610.
24. Mitsudoma, T., Steinberg, S. M., Oie, H. K. et al. Ras gene mutation in non small cell lung cancer are associated with shortened survival irrespective of treatment intent. *Cancer Research* 1991, 51: 4999-5002.
25. Mitsudoma, T., Steinberg, S. M. Nau, M. M. et al. P53 mutation in non small lung cancer cell line and their correlation with the presence of ras mutations and clinical features. *Oncogene* 1992, 7:171-180.
26. D'amico, D., Carbone, D., Mitsudomi, T., et al. High frequency of somatically acquired p53 mutations in small cell lung cancer cell lines and tumors. *Oncogene* 1992, 7:339-346.
27. Brodsky, F. M. and Guagliardi, L. E. The cell biology of antigen processing and presentation. *Annu Rev Immunol* 1991, 9:707.
28. Rudensky, A. Y., Preston-Hulburt, P., Hong. S. C. et al. Sequence analysis of peptides bound to MHC class II molecules. *Nature* 1991, 353-622.
29. Hunt, D. F., Michael H. Dickinson, T. A. et al. Peptides presented to the immune system by the murine class II histocompatibility complex molecule I-A$^d$. *Science* 1992, 256:1817.
30. Eishenlohr, L. C., Yedwell, J. W., and Bennink, J. R. A transient transfection system for identifying biosynthesized proteins processed an presented to class I MHC restricted T lymphocytes. *J. Immunol. Meth.* 1992, 154: 131.
31. Rock, K. L., Rothstein, L. and Benacerraf B. Analysis of the association of peptides of optimal length to class I molecules on the surface of cells. *Proc. Natl. Mad. Sci. USA* 1992, 89:8918.
32. Townsend, A. and Bodmer, H. Antigen recognition by class I-restricted T lymphocytes. *Ann Rev Immunol* 1989, 7:601-24.
33. Rotzschke, O., Falk, K. Deres, K. et al. Isolation and analysis of naturally processed viral peptides as recognized by cytotoxic T cells. *Nature* 1990, 348:252-254.
34. Van Bleek, G., and Nathenson, S. Isolation of an endogenously processed immunodominant viral peptide from the class I H-2K molecule. *Nature* 1990, 348:213-216.
35. Chang, J. C. C., Zhang, T. L. Edgerton, T. L. et al. Heterogeneity in direct cytotoxic function of L3T4 T cells: TH1 clones express higher cytotoxic activity to antigen presenting cells than TH2 clones. *J. Immunol.* 1990, 145: 409.
36. Ozdemirli, M., El-Khatib, L., Bastiani, H. et al. The cytotoxic process of CD4 Th1 clones. *J. Immunol.* 1992, 149:1889.
37. McKisic, M. D., Lancki, D. W., Fitch, F. W. Cytolytic activity of murine CD4$^+$ T cell clones correlates with gamma IFN production in mouse strains having BALB/c background. *J. Immunol.* 1991, 150:3793.
38. De Plaen, E., Lurquin, C., Van P. A., et al. Immunogenic (tum-) variants of mouse tumor P815: cloning of the gene of tum-antigen P91A and identification of the tum-mutation. *Proc Natl Acad Sci USA* 1988, 85: 2274-8.
39. Lurquin, C., Van, P. A. et al. Structure of the gene of tum-transplantation antigen P91A: the mutated exon encodes a peptide recognized with Ld by cytolytic T cells. *Cell* 1989, 58, 293:303.
40. Lorenz, R. G., Tyler, A. N. Allen, P. M. Reconstitution of the immunogenic peptide Rnase (43-56) by identification of the transfer of the critical residues into an unrelated peptide backbone. *J. Exp. Med.* 1989, 170:203.
41. Takahashi, H. S., Merli, S. D., Putney, R. et al. A single amino acid interchange yields reciprocal CTL specificities for HIV-1 gp160. *Science* 1989, 246:116.
42. Romain, N., Gruner, S., Brang, D., Kampgen, E., Lenz, A., et al. Proliferating dendritic cell progenitors in human blood. *J. Exp. Med.* 1994, 180:83-93.
43. Falk, K, Rotzschke, O., Stevanovic, S., Jung, G., Ramrnensee, H-G. Allele-specific motifs revealed by sequencing of self-peptides eluted from MHC molecules. *Nature* 351, 290-296 (1991).
44. Ruppert, J., Sidney, J., Celis, E., Kubo, R. T., Grey, H. M., and Sette, A. Prominent role of secondary anchor residues in peptide binding to HLA-A2.1 molecules. *Cell* 74, 929-937 (1993).

The invention claimed is:

1. An isolated DNA sequence encoding a mutant ras peptide consisting of SEQ ID NO: 11.

2. A plasmid or virus vector comprising the DNA sequence of claim 1.

* * * * *

SEQUENCE LISTING

```
<160> NUMBER OF SEQ ID NOS: 16

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Lys Leu Val Val Val Gly Ala Gly Gly Val Gly Lys Ser
1               5                   10

<210> SEQ ID NO 2
```

```
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 2

Lys Leu Val Val Val Gly Ala Asp Gly Val Gly Lys Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Lys Leu Val Val Val Gly Ala Asp Gly Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Lys Leu Val Val Val Gly Ala Val Gly Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 5

Lys Leu Val Val Val Gly Ala Cys Gly Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Tyr Lys Leu Val Val Val Gly Ala Val
1               5

<210> SEQ ID NO 7
<211> LENGTH: 42
<212> TYPE: DNA
<213> ORGANISM: Artificial Sequence
<220> FEATURE:
<223> OTHER INFORMATION: DNA sequence encoding the peptide of SEQ ID
      NO:12.

<400> SEQUENCE: 7
tataaacttg tggtagttgg agctgatggc gtaggcaaga gt                    42

<210> SEQ ID NO 8
<211> LENGTH: 42
```

-continued

```
<212> TYPE: DNA
<213> ORGANISM: Artificial Sequence
<220> FEATURE:
<223> OTHER INFORMATION: DNA sequence encoding the peptide of SEQ ID
      NO:13.

<400> SEQUENCE: 8
tataaacttg tggtagttgg agcttgtggc gtaggcaaga gt                    42

<210> SEQ ID NO 9
<211> LENGTH: 42
<212> TYPE: DNA
<213> ORGANISM: Artificial Sequence
<220> FEATURE:
<223> OTHER INFORMATION: DNA sequence encoding the peptide of SEQ ID
      NO:10.

<400> SEQUENCE: 9
tataaacttg tggtagttgg agctgttggc gtaggcaaga gt                    42

<210> SEQ ID NO 10
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 10

Tyr Lys Leu Val Val Val Gly Ala Val Gly Val Gly Lys Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 11

Tyr Leu Val Val Val Gly Ala Asp Gly Val
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 12

Tyr Lys Leu Val Val Val Gly Ala Asp Gly Val Gly Lys Ser
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 13

Tyr Lys Leu Val Val Val Gly Ala Cys Gly Val Gly Lys Ser
1               5                   10

<210> SEQ ID NO 14
<211> LENGTH: 10
<212> TYPE: PRT
```

```
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Xaa is Lys or Tyr; If Xaa at position 3 is
      Val, then Xaa at position 1 is Tyr
<220> FEATURE:
<221> NAME/KEY: MISC_FEATURE
<222> LOCATION: (3)..(3)
<223> OTHER INFORMATION: Xaa is any amino acid; If Xaa at position 3 is
      Val, then Xaa at position 1 is Tyr
<220> FEATURE:
<221> NAME/KEY: MISC_FEATURE
<222> LOCATION: (8)..(8)
<223> OTHER INFORMATION: Xaa at position 8 is Asp, Val, Cys, Ala, Arg,
      or Ser

<400> SEQUENCE: 14

Xaa Leu Xaa Val Val Gly Ala Xaa Gly Val
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa at position 1 is Lys or Tyr; if Xaa at
      position 3 is Val, then Xaa at position 1 is Tyr
<220> FEATURE:
<221> NAME/KEY: MISC_FEATURE
<222> LOCATION: (3)..(3)
<223> OTHER INFORMATION: Xaa at position 3 is any amino acid; if Xaa at
      position 3 is Val, then Xaa at position 1 is Tyr
<220> FEATURE:
<221> NAME/KEY: MISC_FEATURE
<222> LOCATION: (8)..(8)
<223> OTHER INFORMATION: Xaa at position 8 is Asp, Val, Cys, Ala, Arg,
      or Ser

<400> SEQUENCE: 15

Xaa Leu Xaa Val Val Gly Ala Xaa Gly Val Gly Lys Ser
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (9)..(9)
<223> OTHER INFORMATION: Xaa at position 9 is Asp, Val, Cys, Ala, Arg,
      or Ser

<400> SEQUENCE: 16

Tyr Lys Leu Val Val Val Gly Ala Xaa
1               5
```